United States Patent [19]
Nishimura et al.

[11] Patent Number: 6,066,470
[45] Date of Patent: *May 23, 2000

[54] METHOD FOR REMOVING N-TERMINAL METHIONINE

[75] Inventors: Osamu Nishimura; Masato Suenaga, both of Hyogo; Hiroaki Ohmae, Nara; Shinji Tsuji, Hyogo, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/872,417

[22] Filed: Jun. 10, 1997

[30] Foreign Application Priority Data

Jun. 14, 1996 [JP] Japan ..................... 8-154634

[51] Int. Cl.⁷ ............... C12P 21/06; C07K 1/107; C07K 1/12
[52] U.S. Cl. .............. 435/69.1; 435/69.4; 435/69.52; 530/300; 530/311; 530/331; 530/343; 530/350; 530/351; 530/399
[58] Field of Search .................. 435/69.1, 69.4, 435/69.52; 530/300, 311, 331, 343, 350, 351, 399

[56] References Cited

FOREIGN PATENT DOCUMENTS 0 329 622 A2  8/1989  European Pat. Off. .

OTHER PUBLICATIONS

Abstract for EP 97 30 3856, dated Sep. 30, 1997, included in European Search Report.

Derwent AN 95–038217 to JP 06 316 557 Nov. 15, 1995.

Caplus Abstract No. 1995: 380330 of JP06316557 Nov. 15, 1994 with Displayed Structures from Reg No.

*Primary Examiner*—Bennett Celsa
*Attorney, Agent, or Firm*—Dike, Bronstein, Roberts & Cushman, LLP; David G. Conlin

[57] ABSTRACT

The present invention provides a method for chemically removing a N-terminal methionine residue selectively, specifically and efficiently from a peptide or a salt thereof having an optionally oxidized methinine residue at its N-terminal. The method reacts a peptide or a salt thereof having an optionally oxidized methinine residue at its N-terminal with an α-diketone derivative, followed by hydrolysis.

14 Claims, 8 Drawing Sheets

Lane 1. hGH 3 μg
Lane 2. blank
Lane 3. molecular weight marker

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (xi) SEQUENCE DESCRIPTION: SEQ ID NO:1:

TATGTACGCG GAGCATAAGA GTCACCGAGG GGAGT          35

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (xi) SEQUENCE DESCRIPTION: SEQ ID NO:2:

ACTCCCCTCG GTGACTCTTA TGCTCCGCGT ACA            33

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:

GATCCCTGGC ATGCA                                              15

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:4:

TATGGATGGG                                                    10

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:5:

AATTCCCATC CA                                                12

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:6:

ATACATATGG ATGGGAATTC CA                                22

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:7:

CCGGATCCTA GTAAAACAAG TCAACTCT                      28

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

TGCCATGAAT TCATGGCA                                    18

METHOD FOR REMOVING N-TERMINAL METHIONINE

TECHNICAL FIELD OF THE INVENTION

The present invention relates to a method for removing an optionally oxidized methionine residue present at the N-terminal of a peptide (including a protein) or a salt thereof.

PRIOR ART

When a protein is synthesized within a cell, its amino terminus is always occupied by methionine, which corresponds to the mRNA initiation condon, i.e. AUG. In naturally produced mature protein molecules, however, that methionine residue is usually no longer present, because it is removed via subsequent processing.

Recent progress in gene recombination technology has made it possible to produce useful proteins using microbes or animal cells, e.g. *Escherichia coli*. In some cases the protein produced retains the methionine described above. For example, in human growth hormone expressed by *Escherichia coli*, the methionine addition rate reaches approximately 100% [Nature, 293, 408 (1981)], and 50% in interferon-α [Journal of Interferon Research, 1, 381 (1981)]. In the production of non-glycosylated human interleukin-2 (rhIL-2) expressed by *Escherichia coli*, in addition to molecule whose initiation amino acid residue is alanine, like natural human interleukin-2, a second molecule with a methionine residue added at the amino terminus (Met-rhIL-2) was found.

Dixon reported in 1964 that DL-alanylglyine when reacted with glyoxylic acid, pyridine and cupric acetate produced pyruvoylglycine by transamination [Biochememistry Journal, 92, 661 (1964)]. Moreover, Dixon reported that thus obtained pyruvoylglycine was reacted with thiosemicarbazide to produce glycine by splitting an amide linkage [Biochemistry Journal, 90, 2C (1964)]. Furthermore, Dixon reported that the above described chemical reaction was applied to Pseudomonas cytochrome C-551 and the N-terminal glutamic acid was removed [Biochemistry Journal, 94, 463 (1965)].

However, the reactions reported by Dixon relate to removal of a N-terminal amino acid of synthesized peptide or mature protein and there is no report in the more than 30 years following this report that the above described chemical reaction might be useful for removal of the N-terminal methionine added to a protein produced by gene recombination technology.

It can be hypothesized that the three dimensional structure, bioactivity and stability-may differ between a molecule with methionine at its amino terminus and one without methionine, even though both molecules are otherwise the same protein; addition of methionine at the amino terminus is believed to possibly cause an increase in protein antigenicity. Therefore, it would be important, in industrial application, to establish a relatively simple and efficient method of selectively removing such amino terminal methionine.

In prior methods for solving this problem, a process was suggested by which methionine could be removed by cyanogen bromide (BrCN) cleavage [Science, 198, 1056 (1977)]; however, no satisfactory result has been obtained, since the process not only premises the absence of other methionine residue(s) in the molecule of the required mature protein but also subjects the protein to a drastic chemical reaction.

A chemical method which makes it possible to remove a N-terminal methionine residue selectively and efficiently from a peptide or protein having a methionine residue at its N-terminal irrespective of kinds of peptide or protein is presently unknown. This fact is thought to be caused by the difficulty in finding an appropriate chemical reaction for removing a N-terminal methionine under mild conditions without denaturing a peptide or protein which is a final product. In particular, in case of the removing an extra N-terminal methionine added to a protein which has a relatively high molecular weight, and is produced by gene recombination technology particularly, aimed for a medical use, it is required not to lower an activity of the protein after removal of the methionine. Thus, it is usually necessary to proceed such reaction in a weakly acidic to basic solution without heating. Therefore, in the state of the arts, good reaction conditions have not been reported, since a lot of limitations are required for the chemical reaction.

SUMMARY OF THE INVENTION

The present inventors, after studying how to provide a method for producing a protein having a natural type amino acid sequence by selectively removing a N-terminal methionine in a protein produced by gene recombination technology, found a method for removing a N-terminal methionine from a protein having an additional methionine by converting a methionine in the protein having the additional methionine to an α-diketone and further by reacting the α-diketone with an organic diamine derivative, thereby, obtaining a peptide or protein having no additional methionine at its N-terminal. The present method for obtaining the peptide or protein is characterized by reacting a peptide or protein having an additional methionine represented by the following formula (I) with a glyoxylic acid as an α-diketone derivative, a cupric sulphate being capable of giving a transition metal ion and a pyridine as an amine derivative to carry out transamination and convert methionine to α-diketone, followed by subjecting the obtained α-diketone derivative to hydrolysis with an o-phenylenediamine as a diamine derivative and also characterized by removing the N-terminal methionine from the peptide or protein having the additional methionine without lowering the activity of the peptide or protein.

The finding was followed by further research, leading to the completion of the present invention.

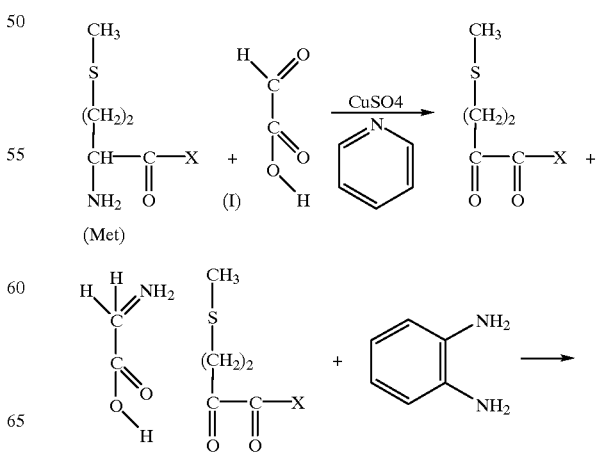

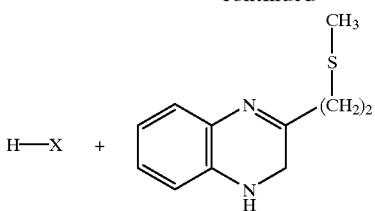

In the formula (I), X represents either an amino acid residue or a peptide chain having two or more amino acids. Preferably, X represents a peptide chain which is a part of a protein produced by gene recombination technology. Furthermore, the peptide or protein consisting of multiple amino acids may be either glycosylated or non-glycosylated one.

That is, the present invention relates to (1) a method for removing a N-terminal optionally oxidized methionine residue, which comprises reacting a peptide or a salt thereof having said methionine residue at its N-terminal with an α-diketone derivative and then subjecting the obtained product to hydrolysis;

(2) a method of the above (1), wherein the peptide having an optionally oxidized methionine residue at its N-terminal is a protein produced by gene recombination technology;

(3) a method of the above (2), wherein the peptide produced by gene recombination technology has at least 30 amino acid residues. One preferred group of peptides is growth hormone, neurotrophin-3, betacellulin, parathyroid hormone or interleukin-2 each having an optionally oxidized methionine residue at its N-terminal;

(4) a method of the above (1), wherein the α-diketone derivative is reacted in the presence of a transition metal ion;

(5) a method of the above (1), wherein the α-diketone derivative is reacted in the presence of a base;

(6) a method of the above (1), wherein the α-diketone derivative is reacted in the presence of a transition metal ion and a base;

(7) a method of the above (1), wherein the α-diketone derivative is glyoxylic acid or a salt thereof;

(8) a method of the above (4), wherein the transition metal ion is a copper ion;

(9) a method of the above (5), wherein the base is a pyridine;

(10) a method of the above (1), wherein the hydrolysis is carried out with using a base;

(11) a method of the above (10), wherein the base is an amine derivative;

(12) a method of the above (10), wherein the base is a diamine derivative, or a thio- or seleno-semicarbazide derivative;

(13) a method of the above (12), wherein the diamine derivative is an o-phenylenediamine;

(14) a method for producing human growth hormone or a salt thereof, which comprises reacting human growth hormone or a salt thereof having a methionine at its N-terminal which is produced by gene recombination technology with a glyoxylic acid or a salt thereof in the presence of a cupric sulphate and a pyridine, and then reacting with an o-phenylehediamine;

(15) a method for producing neurotrophin-3 or a salt thereof, which comprises reacting neurotrophin-3 or a salt thereof having a methionine at its N-terminal which is produced by gene recombination technology with a glyoxylic acid or a salt thereof in the presence of a cupric sulphate and a pyridine, and then reacting with an o-phenylenediamine.

(16) a method for producing human betacellulin or a salt thereof, which comprises reacting human betacellulin or a salt thereof having a methionine at its N-terminal which is produced by gene recombination technology with a glyoxylic acid or a salt thereof in the presence of a cupric sulphate and a pyridine, and then reacting with an o-phenylenediamine.

(17) a method for producing human interleukin-2 or a salt thereof, which comprises reacting human interleukin-2 or a salt thereof having a methionine at its N-terminal which is produced by gene recombination technology with a glyoxylic acid or a salt thereof in the presence of a cupric sulphate and a pyridine, and then reacting with an o-phenylenediamine;

(18) a method for producing parathyroid hormone or a salt thereof, which comprises reacting parathyroid hormone or a salt thereof having a methionine at its N-terminal which is produced by gene recombination technology with a glyoxylic acid or a salt thereof in the presence of a cupric sulphate and a pyridine, and then reacting with an o-phenylenediamine;

(19) a compound of the formula:

$$CH_3-S(O)_m-(CH_2)_2-CO-CO-X$$

wherein m is an integer from 0–2 and X is an amino acid residue or a peptide chain, or a salt thereof; and

(20) a method for producing an amino acid, a peptide, a protein or a salt thereof, which comprises subjecting the compound of the above (19) to hydrolysis; etc.

DETAILED DESCRIPTION OF THE INVENTION

Figure 1:
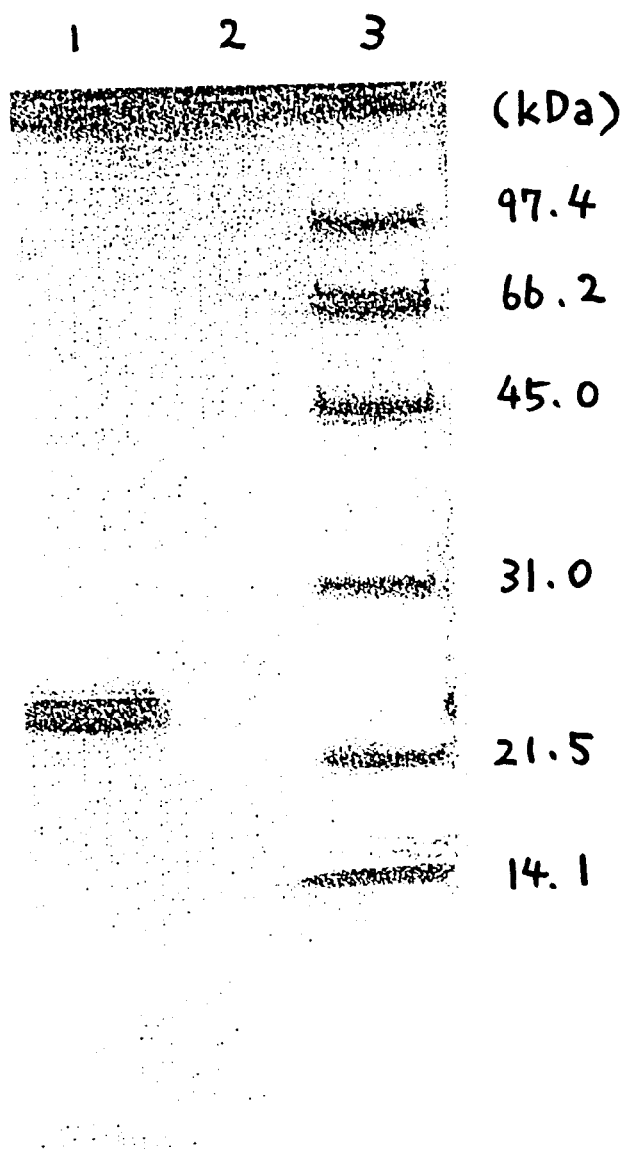
FIG. 1 shows the result of the electrophoresis obtained in Working Example 2a).

As used herein, an optionally oxidized methionine residue represents either a methionine residue or that residue having an oxidized sulfur, wherein the methionine having an oxidized sulfur represents a sulfoxide or sulfone group.

For example, a peptide having an optionally oxidized methionine residue at its N-terminal may be a peptide of the formula:

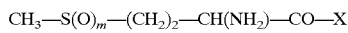

wherein m is an integer from 0–2 and X is an amino acid residue or a peptide chain. These peptides may be in the form of salt. Any salt may be used which does not inhibit the present reaction. Among them, a pharmaceutically acceptable salt is preferable. For example, a salt with an iorganic acid such as hydrochloride, hydrobromic acid, nitrate, sulfate, phosphate, etc.; a salt with an organic acid such as acetate, phtalate, fumarate, tartarate, maleate, citrate, succinate, methanesulfonate, p-toluenesulfonate, etc.; a salt with an alkali metal such as sodium salt, potassium salt, etc.; a salt with an alkaline earth metal salt such as calcium salt, etc.; or an ammonium salt, etc.; is preferably used.

In the above formula, m is preferably 0 and X is preferably a peptide chain whose number of amino acids is not less than 2.

A peptide to be used for the present removing method may be either a usual peptide whose number of amino acid is less than 50 or a so called protein whose number of amino acid is not less than 50. Thus, in the present specification, the term "peptide" includes not only molecules having less than 50 amino acids but also those having 50 or more amino acids. Preferably, molecules (so called protein) having 50 or more amino acids are used as a peptide.

For example, the peptide more preferably include peptides having from 2 amino acids to 1000 amino acids, even more preferably 15 amino acids to 500 amino acids. A preferred group of peptides include the following molecules:

growth hormone (GH), parathyroid hormone (PTH), insulin, nerve growth factor, brain-derived neurotrophic factor, ciliary neurotrophic factor, glial derived neurotrophic factor, neurotrophin-3, 4 or 6, central nerve growth factor, gliocyte growth factor, lung-derived neurotrophic factor, epidermal growth factor, fibroblast growth factor, platelet-derived growth factor, transforming growth factor α or β, endothelial cell growth factor, tissue plasminogen activator, urokinase, protein C, thrombomodulin, bone morphogenetic protein, calcitonin, insulin-like growth hormone, interferon-α, β or γ, interleukin-1(α,β) to 12, granulocyte colony stimulating factor, granulocyte macrophage colony stimulating factor, granulocyte macrophage stimulating factor, thrombopoietin, somatomedin C, erythropoietin, PACAP, atrial natriuretic peptide, endothelin, megakaryocyte growth factor, hematopoietic stem cell growth factor, hepatocyte growth factor, motilin, immunotoxin, tumor necrosis factor, hirudine, corticotropin, angiotensin, angiotensin 2 and angiotensin 2-antagonistic peptides, angiotensin 3, bradykinin derivatives, bradykinin enhancing factor, α, β or γ endorphin, enkephalin, neutrophil chemotactic factor, gastrin, glucagon, growth hormone-releasing factor, kyotorphin, kallidin, gonadotropic hormone releasing hormone, mast cell degranulating peptide, melanocyte stimulating hormone, neurotensin, trypsin inhibitor, oxytocin, proinsulin C-peptide, secretin, somatostatin, thyroid-stimulating hormone releasing hormone, ubiquitin, urogastrone, vasopressin derivatives, kinin derivatives, tuftsin, somatomedin, corticotropin releasing factor, insulin-like growth factor, calcitonin gene related peptide, PTHrP, VIP, DHI, insulinotropin, GRP, CCK-PZ, Galanin, Antrum Peptide, motilin, PPY, Pancreatic Polypeptide, PSP, pancreastatin, hCG, hCS, relaxin, serum thymic factor, thymopoietin, thymosin, Factor XIII, Factor VIII, prourokinase, SOD, Factor VIIa, antithrombin, or their muteins (which show the same or more biological or immunological activity as a natural protein and which are characterized in that one or more amino acid of the natural protein is substituted, deleted or added); or a chemically synthesized known or novel peptide. Among them, a peptide produced by gene recombination technology, in particular, growth hormone, neurotrophin-3, betacellulin, parathyroid hormone, interleukin-2, etc. which is produced by gene recombination technology and which has an additional optionally oxidized methionine at its N-terminal is even more preferably used.

The above-described natural peptides may be derived from any animal species. Those derived from a human are preferably used.

In the present specification, an α-diketone derivative may be any one which can cause transamination of the above described peptide or a salt thereof. For example, there is used a compound of the formula: $R^1$—CO—CO—$R^2$ wherein $R^1$ represents a hydrogen, or a lower alkyl or phenyl group which may be substituted by a carboxyl group ($R^1$ is preferably a hydrogen or a methyl, more preferably a hydrogen); and $R^2$ represents a hydroxyl group, a lower alkoxy group or an amino group which may be substituted by a lower alkyl ($R^2$ is preferably a hydroxyl group); or a salt thereof.

In the above formula, as a lower alkyl group represented by $R^1$, an alkyl group having about 1 to 6 carbon atoms such as methyl, ethyl, propyl, i-propyl, butyl, i-butyl, sec-butyl, t-butyl, etc. is used, and as a lower alkoxy group represented by $R^2$, an alkoxy group having about 1 to 6 carbon atoms such as methoxy, ethoxy, propoxy, i-propoxy, butoxy, i-butoxy, sec-butoxy, t-butoxy, etc. is used. Moreover, as an amino group which may be substituted by a lower alkyl group, an amino group which may have one to two lower alkyl groups as described above is used. Furthermore, as a salt of the compound of the formula, there is used a salt similar to that of the peptide as described above.

An α-diketone derivative is exemplified by glyoxylic acid, pyruvic acid, oxalacetic acid, phenylglyoxylic acid, 2-oxoglutaric acid, etc. Among them, glyoxylic acid is preferably used.

The transamination reaction between a peptide or a salt thereof having an optionally oxidized methionine residue at its N-terminal and an α-diketone derivative is preferably carried out for about 5 minutes to 2 hours (more preferably about 15 minutes to 1 hour) at about 0 to 70° C. (more preferably 20 to 40° C.) with usually using about 1 to 10,000 moles (more preferably about 2,000 to 4,000 moles) of the α-diketone derivative relative to one mole of the peptide or a salt thereof. Any buffer solution (e.g. phosphate buffer, acetate buffer, citrate buffer, etc.) may be used for the above described transamination reaction, as long as it does not inhibit the reaction. Among others, acetate buffer is preferably used. The reaction pH is preferably adjusted in the range of about 2 to 9, more preferably about 4 to 7, even more preferably about 5 to 6 to process the reaction under the conditions which do not denature the peptide or a salt thereof having an optionally oxidized methionine residue at its N-terminal.

In order to enhance the reaction, it is preferable to react the α-diketone derivative in the presence of a transition metal ion. Usually, it is preferable to use about 0.01 to 0.1 mole (more preferably 0.01 to 0.05 mole) of the transition metal ion relative to one mole of the α-diketone derivative. The transition metal ion includes, for example, copper ion ($Cu^+$, $Cu^{2+}$), cobalt ion ($Co^{2+}$, $Co^{3+}$), nickel ion ($Ni^{2+}$, $Ni^{3+}$), iron ion ($Fe^{2+}$, $Fe^{3+}$), zinc ion ($Zn^{2+}$), aluminum ion ($Al^{3+}$), manganese ion ($Mn^{2+}$, etc.), gallium ion ($Ga^{3+}$), indium ion ($In^{3+}$), magnesium ion ($Mg^{2+}$), calcium ion ($Ca^{2+}$), etc. Among others, copper ion and cobalt ion are more preferable and, in particular, copper ion ($Cu^{2+}$) is preferable. These transition metal ions are preferably added to the reaction solvent in the form of a salt with an inorganic acid such as sulfonic acid, nitric acid, hydrochloric acid, perchloric acid, etc. or an organic acid such as acetic acid, oxalic acid, citric acid, carbonic acid, etc. Among others, copper sulfate and copper acetate are preferably used and, in particular, cupric sulfate is more preferably used.

The peptide or a salt thereof having an optionally oxidized methionine residue at its N-terminal is preferably reacted with an α-diketone derivative in the presence of a base. Usually, about 0.1 to 2 moles (preferably about 0.5 to 1.0 mole) of a base are preferably used relative to one mole of an α-diketone derivative. As a base, an organic base including an alkylamine derivative such as triethylamine, tributylamine, etc., an aromatic amine derivative such as N,N-dimethylaniline, pyridine, lutidine, collidine, 4-(dimethylamino)pyridine, imidazole, etc., and urea can be used. Among others, an aromatic amine derivative is preferable, in particular, pyridine is more preferably used.

Moreover, the above-mentioned transamination reaction is preferably carried out by subjecting the peptide or a salt thereof having an optionally oxidized methionine residue at its N-terminal to the reaction with an α-diketone derivative in the presence of a transition metal ion and a base. Practically, a solution comprising three components consisting of a transition metal ion, a base and an α-diketone derivative (e.g. copper sulfate, pyridine and glyoxylic acid, etc.) is added to a solution comprising the peptide or a salt thereof having an optionally oxidized methionine residue at its N-terminal to proceed the transamination reaction.

A compound or a salt thereof of the formula: $—CH_3—S(O)_m—(CH_2)_2—CO—CO—X$ wherein m is an integer from 0 to 2 and X is an amino acid residue or a peptide chain, which is obtained by said transamination reaction, is a novel compound and can be isolated and purified from a reaction solution by a conventional purification method such as extraction, salting-out, distribution, recrystallization, chromatography, etc. or can be subjected to the next hydrolysis reaction without any isolation or purification.

The diketone derivative obtained by the transamination reaction is usually subjected to hydrolysis with a base to obtain a peptide or a salt thereof from which an optionally oxidized methionine residue is removed at its N-terminal.

As a base used for the hydrolysis reaction, for example, an amine including cysteamine, an alkylamine such as triethylamine, tributylamine, etc., an aromatic amine such as N,N-dimethyl-aniline, pyridine, lutidine, collidine, 4-(dimethyl-amino)pyridine, imidazole, etc., a diamine such as o-phenylenediamine, tolylene-3,4-diamine, 3,4-diaminobenzoic acid, 2,3-diaminophenol, 4-chloro-o-phenylenediamine (preferably an aromatic diamine, more preferably an o-phenylenediamine), etc., a thiosemicarbazide such as acetonethiosemi-carbazide, phenylthiosemicarbazide, etc., a seleno-semicarbazide such as selenosemicarbazide, acetoneselenosemicarbazide, etc. are exemplified. Among others, an amine is preferable, and a diamine and a thiosemicarbazide are more preferable. In particular, o-phenylenediamine is even more preferably used.

An amount of the base is usually from about 1 to 10,000 moles (preferably from about 500 to 2,000 moles) relative to one mole of the diketone derivative. The hydrolysis reaction is preferably carried out for about 1 to 50 hours (preferably for about 10 to 25 hours) at temperatures ranging from about 0 to 70° C. (preferably from about 20 to 40° C.). The reaction is preferably carried out with using a buffer solution as a solvent. The buffer solution is exemplified by phosphate buffer solution, acetate buffer solution, citrate buffer solution, etc. Any buffer solution may be used for the above described transamination reaction, as long as it does not inhibit the reaction. Among others, acetate buffer is preferably used. Reaction pH is preferably adjusted in the rage of about 2 to 9, more preferably about 3 to 7, still more preferably about 4 to 6 neighboring neutral condition to process the reaction under the conditions which do not denature the obtained peptide or a salt thereof.

The obtained peptide or a salt thereof can be isolated and purified from the reaction solution by using a conventional purification method such as extraction, salting-out, distribution, recrystallization, chromatography, etc. or can be subjected to the next hydrolysis reaction without any isolation or purification. A preferable purification method is exemplified by using ion exchange chromatography, etc. through SP-Sepharose (Pharmacia Biotech) or DEAE-5PW (Tosoh).

Since a polypeptide produced by the present invention does not have a methionine at its N-terminal and it has the same amino acid sequence as natural bioactive polypeptide, it exhibits an activity equal to that of natural polypeptide and its toxicity is low; it can therefore be used safely as a drug and a diagnosis reagent. The present invention provides a method for specific removal of the N-terminal methionine from methionylpeptide.

In the specification and drawings of the present invention, amino acid abbreviations are based on those recommended by the IUPAC-IUB Commission on Biochemical Nomenclature, or those used commonly in the related field.

Examples are shown below (abbreviation represents L-type unless otherwise specified):

SDS: Sodium dodecylsulfate
Gly: Glycine
Ala: Alanine
Val: Valine
Leu: Leucine
Ile: Isoleucine
Ser: Serine
Thr: Threonine
Cys: Cystein
Met: Methionine
Glu: Glutamic acid
Gln: Glutamine
Asp: Aspartic acid
Asn: Asparagine
Lys: Lysine
Arg: Arginine
His: Histidine
Phe: Phenylalanine
Tyr: Tyrosine
Trp: Tryptophan
Pro: Proline
Asx: Asp+Asn
Glx: Glu+Gln

EXAMPLES

The present invention is described in detail by means of the following reference examples and working examples, which, however, serve merely to illustrate the embodiments of the invention but not to restrict the invention.

Reference Example 1

Production of Met-rhGH:

Met-rhGH was produced according to the method described in Reference Example 4 of Japanese Patent Publication Laid-open No. 171699/1987.

(i) Producer:

Transformant *Escherichia coli* K12 χ 1776/pHGH107 (ATCC 31538) was employed.

(ii) Cultivation:

*Escherichia coli* K12 χ 1776/pHGH107(ATCC 31538, IFO 14505) was inoculated into a 2 l capacity of flask containing 1 liter of a liquid seed medium (pH 7.0) comprising 1% Bacto-tryptone, 0.5% Bacto-yeast, 0.5% sodium chloride, 10 mg/l tetracycline hydrochloride, 10 mg/l sodium ampicillin, 20 mg/l thymine and 100 mg/l diaminopymeric acid, and then subjected to rotary shaking cultivation at 37° C. overnight. The resultant culture liquid was then transferred to a 50 liter jar fermentor containing 20 liter of a liquid production medium (pH 6.8) containing 1.68% sodium hydrogen phosphate, 0.30% potassium dihydrogenphosphate, 0.10% ammonium chloride, 0.05% sodium chloride, 200 mg/l antifoaming agent, 1.00% glucose, 1.00% casamino acid, 246 mg/l magnesium sulfate, 10 mg/l tetracycline hydrochloride, 10 mg/l sodium ampicillin, 20 mg/l thymine and 100 mg/l diaminopimeric acid, after which it was subjected to cultivation under aeration and agitation at 37° C. for 10 hours. The thus obtained culture fluid was subjected to centrifugation to harvest bacterial cells.

Reference Example 2

To 2 kg of wet cells obtained in Reference Example 1 was added 6 L of 50 mM Tris-HCl buffer (pH 8.0) containing 8 M guanidine hydrochloride. The mixtures were stirred to dissolve the cells in the buffer solution, followed by centrifugation (10,000 rpm, 60 minutes) to obtain 6 L of cell extract solution. Thus obtained solution was dialyzed twice against about 70 L of 10 mM Tris-HCl (pH 7.0). After dialysis, to about 9 L of dialyzed solution was added ammonium sulfate to give a final concentration of 20% saturation, followed by centrifugation (4,200 rpm, 60 minutes) to obtain about 10 L of supernatant. Each half volume of this supernatant was allowed to pass through Phenyl-Toyopearl 650C column (5 cmφ×50 cm), followed by adsorption and washing on the column. The fraction of Met-rhGH was collected by eluting with a linear concentration gradient consisting of 10 mM Tris-HCl buffer solution (pH 7.0) containing 40% saturated ammonium sulfate and 10 mM Tris-HCl buffer solution (pH 7.0) and was dialyzed against 50 mM sodium hydrogen carbonate (pH 8.2), followed by centrifugation (4,200 rpm, 45 minutes) to obtain about 3.7 L of supernatant. Each one-forth volume of this supernatant was allowed to pass through DEAE-Toyopearl 650M column (4 cm φ×50 cm), followed by adsorption and washing on the column. The fraction of Met-rhGH was collected by eluting with a linear concentration gradient consisting of 10 mM sodium hydrogen carbonate buffer solution (pH 8.2) and 10 mM sodium hydrogen carbonate buffer solution (pH 8.2) containing 1 M sodium chloride and was dialyzed against 50 mM sodium hydrogen carbonate (pH 8.2). About 1.2 L of the dialyzed solution was allowed to pass through DEAE-5PW column (55 mm φ×20 cm, Tosoh), followed by adsorption and eluting with HPLC using a linear concentration gradient consisting of 10 mM sodium hydrogen carbonate buffer solution (pH 8.2) and 10 mM sodium hydrogen carbonate buffer solution (pH 8.2) containing 1 M sodium chloride and was dialyzed against 50 mM sodium hydrogen carbonate (pH 8.2), to obtain about 600 ml of the fraction of Met-rhGH. This solution was concentrated to about 294 ml using Amicon Diaflow (YM-10 membrane, 76 mm φ, Amicon) and subjected to gel filtration using Toyopearl HW-50F (8 cm φ×50 cm) column equilibrated with 100 mM sodium hydrogen carbonate (pH 8.2) to obtain the fraction of Met-rhGH. The fraction was filtered with MILLEX-GV filter (0.22 µl, Milipore) to obtain 869 mg of Met-rhGH.

Working Example 1

Fifty mg of human growth hormone having methionine at its N-terminal (Met-rhGH) obtained in Reference Example 2 was dissolved in 40 ml of 50 mM phosphate buffer solution (pH 8.0). To the mixture was added a solution containing 0.1 M copper sulfate 5 ml, glyoxylic acid 2.3 g and pyridine 5 ml, and allowed to stand at 25° C. for 1 hour. The reaction solution was passed through Sephadex G-25 column (25 mmID×600 mmL) equilibrated with 2M acetate-2M sodium acetate buffer solution and the column was washed with the same buffer solution at 6 ml/minute of flow rate to collect the fraction of diketone derivative of Met-rhGH. To this fraction was added o-phenylenediamine to give a final concentration of 20 mM, followed by vacuum and sealing with nitrogen gas, and the reaction proceeded at 37° C. for 20 hours. The reaction solution was passed through Sephadex G-25 column (25 mmID×600 mmL) equilibrated with 20 mM Tris-HCl buffer solution (pH 8.0) and the column was washed with the same buffer solution at 6 ml/minute of flow rate to collect the fraction of human growth hormone having no methionine at its N-terminal (rhGH). The collected fraction was loaded on DEAE-5PW column (21.5 mmID×150 mmL) equilibrated with 20 mM Tris-HCl buffer solution (pH 8.0), followed by eluting with a linear concentration gradient of 0–100% solution B (B=20 mM Tris-HCl buffer solution +1 M sodium chloride, pH 8.0) at 8.5 ml/minute of flow rate for 30 minutes to collect the fraction of rhGH. The collected fraction was passed through Toyopearl HW-50 column (20 mmID×600 mmL) (Tosoh Corporation) equilibrated with 5% ethanol solution, followed by eluting with the same solution at 6 ml/minute of flow rate to collect the fraction of rhGH. The collected fraction was subjected to freeze drying to obtain rhGH powder.

Working Example 2

(Determination of Feature of rhGH)

a) Analysis with SDS-polyacrylamide Gel Electrophoresis

The powder of rhGH obtained in Working Example 1 was suspended in Sample buffer [Laemmli, Nature, 227, 680 (1970)] and the mixture was heated with 100 mM DTT at 100° C. for 1 minutes, followed by electrophoresis with Multi Gel 10/20 (Daiichi Pure Chemicals Co., Ltd.). After electrophoresis, the gel was stained with Coomassie brilliant blue and only one single band of the purified protein was obtained. The results are shown in FIG. 1. In FIG. 1, Lanes 1–3 represent rhGH (3 µg), blank and molecular weight markers, respectively.

b) Analysis of N-terminal Amino Acid Sequence

The N-terminal amino acid sequence of rhGH obtained in Working Example 1 was determined using a gas-phase protein sequencer (Applied Biosystems, 477A model).

The N-terminal amino acid sequence of rhGH obtained in Working Example 1 agreed with that pridicted from cDNA sequence of rhGH. The results are shown in Table 1.

TABLE 1

Analysis of N-terminal amino acid sequence

| Residue No. | PTH[1])-amino acid detected | amino acid predicted from cDNA sequence of rhGH |
|---|---|---|
| 1 | Phe | Phe |
| 2 | Pro | Pro |
| 3 | Thr | Thr |
| 4 | Ile | Ile |
| 5 | Pro | Pro |
| 6 | Leu | Leu |
| 7 | Ser | Ser |
| 8 | Arg | Arg |
| 9 | Leu | Leu |
| 10 | Phe | Phe |
| 11 | Asp | Asp |
| 12 | Asn | Asn |
| 13 | Ala | Ala |
| 14 | Met | Met |
| 15 | Leu | Leu |
| 16 | Arg | Arg |
| 17 | Ala | Ala |
| 18 | His | His |
| 19 | Arg | Arg |
| 20 | Leu | Leu |

Analysis was carried out using 1 nmol of rhGH.
[1])phenylthiohydantoin c) Analysis of Amino Acid Composition About 20 μg of rhGH obtained in Working Example 1 was used for the determination of amino acid composition with amino acid analyzer (Beckman 6300E system). The amino acid composition of rhGH obtained in Working Example 1 agreed with that predicted from cDNA sequence of rhGH. The results are shown in Table 2.

TABLE 2

Analysis of amino acid composition

| Amino acid | Number of residues per 1 mole | Values predicted from cDNA sequence of rhGH |
|---|---|---|
| Asx | 19.4 | 20 |
| Thr[1]) | 9.9 | 10 |
| Ser[1]) | 16.9 | 18 |
| Glx | 27.0 | 27 |
| Pro | 7.8 | 8 |
| Gly | 7.7 | 8 |
| Ala | 6.9 | 7 |
| Cys[2]) |  | 4 |
| Val | 6.8 | 7 |
| Met | 3.2 | 3 |
| Ile | 7.3 | 8 |
| Leu | 24.8 | 26 |
| Tyr | 7.6 | 8 |
| Phe | 12.4 | 13 |
| His | 2.9 | 3 |
| Lys | 9.0 | 9 |
| Arg | 10.3 | 11 |
| Trp[2]) |  | 1 |

Acid hydrolysis (6N HCl, 1% phenol, 110° C., Mean value of those obtained after 24 and 48 hours of hydrolysis)
[1])Value extrapolated on the assumption that hydrolysis time was 0 hours.
[2])Undetected d) Analysis of C-terminal Amino Acid About 15 nmol of rhGH obtained in Working Example 1 was used for the determination of C-terminal amino acid with amino acid analyzer (Beckman 6300E system). The C-terminal amino acid of rhGH obtained in Working Example 1 agreed with that predicted from cDNA sequence of rhGH. The results are shown in Table 3.

TABLE 3

Analysis of C-terminal amino acid

| rhGH | C-terminal amino acid | Yield (%) |
|---|---|---|
|  | Phe | 55.4 |

Vapor-phase Hydrazinolysis (100° C., 3.5 hours)

Working Example 3
(Determination of rhGH activity)

An assay of rhGH purified and obtained in Working Example 1 was carried out using Nb 2 cells according to the method described in Journal of Endocrinology & Metabolism, 51, 1058 (1980) and revealed that rhGH purified and obtained in Working Example 1 had an activity almost similar to a standard product.

Reference Example 3
Production of Met-NT-3:

Met-NT-3 was produced according to a method described in Reference Examples 1–3 and Working Examples 1–2 of the specification of Japanese Patent Application No. 74775/1996.

(1) Cloning of NT-3 DNA

E. coli Y1090 was infected with λ gt 11 cDNA library (Clontech Laboratories, Inc.) derived from human glioma and about $6 \times 10^5$ of phages were inoculated into NZCY medium (Molecular Cloning, A Laboratory Manual, Cold Spring Harbor Laboratory, 1982) and cultivated at 37° C. for 5 hours. A nylon membrane was placed on the plate, allowed to stand for 1 minute and removed from the plate. This nylon membrane was put in a solution of 0.5M NaOH-1.5M NaCl, in a solution of 1.5M NaCl-0.5M Tris-Hcl (pH 8.0) and in a solution of 2×SSC (Molecular Cloning, A Laboratory Manual, as described above), in this order, followed by drying and allowing to stand at 80° C. for 2 hours.

DNA (about 0.38 kb) coding human β NGF [Nature, 303, 821 (1983)] was chemically synthesized and a probe was prepared by labeling the DNA with [α-$^{32}$P]dCTP according to nick translation.

The obtained nylon membrane and probe were hybridized according to a method described in Molecular Cloning, A Laboratory Manual, Cold Spring Harbor Laboratory, 1982. That is, the nylon membrane was put in a hybridization solution containing the probe and allowed to stand at 65° C. for 16 hours. Said nylon membrane was washed with 2×SSC-0.1% SDS at room temperature and thereafter with 1×SSC-0.1% SDS at 60° C., followed by auto radiography to obtain a positive clone. The cDNA digested with EcoRI from the obtained clone λβ GN1321 was inserted into EcoRI site of plasmid pUC118 (Takara Shuzo Co., Ltd.) to obtain plasmid pUNK5.

(2) Construction of NT-3 Expression Vector for E.coli

In the NT-3 cDNA inserted in plasmid pUNK5 obtained in Reference Example 3(1), there are a ScaI site close to the region coding Tyr of the 11th amino acid from the N-terminal of NT-3 and a NsiI site close to the region 50 bases downstream from the stop codon of NT-3. Thus, a ScaI-NsiI fragment was isolated from plasmid pUNK5 to which adapters NGFTE-1 (35 mer), NGFTE-2 (33 mer), NGFTE-3 (7 mer) and NGFTE-4 (15 mer) were ligated with T4 DNA ligase, followed by treatment of NdeI and BamHI to obtain 0.3 kb NdeI-BamHI fragment.

Said adapters are shown below.
NGFTE-1: 5' TATGTACGCGGAGCATAAGAGTCAC-CGAGGGGAGT 3' 35 mer (Sequence ID Number: 1)

NGFTE-2: 5' ACTCCCCTCGGTGACTCTTATGCTC-
CGCGTACA 3' 33 mer (Sequence ID Number: 2)
NGFTE-3: 5' TGCCAGG 3' 7 mer
NGFTE-4: 5' GATCCCTGGCATGCA 3' 15 mer (Sequence ID Number: 3)

Expression vector pET-3C having T7 promoter [Rosenberg et al., Gene, 56, 125 (1987)] was digested with NdeI and BamHI to obtain 4.4 kb NdeI-BamHI fragment.

The obtained 4.4 kb NdeI-BamHI fragment and 0.3 kb NdeI-BamHI fragment were ligated with T4 DNA ligase, followed by transformation *Escherichia coli* DH1. From the obtained ampicillin resistant transformant (*Escherichia coli* DH1/pENGFT103) was isolated plasmid pENGFT103.

(3) Production of Met-NT-3 in *E. coli*

Using NT-3 expression vector pENGFT103 obtained in Reference Example 3(2) and T7 lysozyme expression vector pLysS, *Escherichia coli* MM294 (DE3) [Molecular Endocrinology, 4, 869 (1990)] was transformed to obtain *Escherichia coli* MM294 (DE3)/pLysS, pENGFT103(IFO 15932, FERM BP-5483).

*Escherichia coli* MM294 (DE3)/pLysS, pENGFT103 (IFO15932, FERM BP-5483) was inoculated into a 2 liter capacity of flask containing 1 liter of LB medium [1% peptone, 0.5% yeast extract, 0.5% sodium chloride] comprising 50 µg/ml ampicillin and 15 µg/ml chloramphenicol, and then subjected to rotary shaking cultivation at 30° C. for 8 hours. The resultant culture liquid was then transferred to a 50 liter jar fermentor containing 20 liter of a liquid production medium [1.68% sodium hydrogen phosphate, 0.3% potassium dihydrogenphosphate, 0.1% ammonium chloride, 0.05% sodium chloride, 0.05% magnesium sulfate, 0.02% antiforming agent, 0.00025% ferrous sulfate, 0.0005% thiamine hydrochloride, 1.5% glucose, 1.5% casamino acid], after which it was subjected to cultivation under aeration and agitation at 30° C. When the Klett value of the culture liquid became about 500, 100 mg/L/minute of isopropyl-β-D-thiogalactopyronoside (IPTG) was added to the medium and the cultivation was further continued for 7 hours. The culture liquid was centrifuged to obtain about 340 g of wet cells which were frozen at −80° C.

(4) Production of Met-NT-3 in *E. coli* (mass production)

*Escherichia coli* MM294 (DE3)/pLysS, pENGFT103 (IFO 15932, FERM BP-5483) was inoculated into a 2 liter capacity of flask containing 1 liter of LB medium [1% peptone, 0.5% yeast extract, 0.5% sodium chloride] comprising 50 µg/ml ampicillin and 15 µg/ml chloramphenicol, and then subjected to rotary shaking cultivation at 30° C. for 16.5 hours. The resultant culture liquid was then transferred to a 50 liter jar fermentor containing 20 liter of LB medium [0.02% antiforming agent, 50 µg/ml ampicillin and 15 µg/ml chloramphenicol], after which it was subjected to cultivation under aeration and agitation at 30° C. for 7 hours. The resultant culture liquid was then transferred to a 500 liter jar fermentor containing 360 liter of a liquid production medium [1.68% sodium hydrogen phosphate, 0.3% potassium dihydrogenphosphate, 0.1% ammonium chloride, 0.05% sodium, chloride, 0.05% magnesium sulfate, 0.02% antifoaming agent, 0.00025% ferrous sulfate, 0.0005% thiamine hydrochloride, 1.5% glucose, 1.5% casamino acid], after which it was subjected to cultivation under aeration and agitation at 30° C. When the Klett value of the culture liquid became about 500, 100 mg/L/minute of isopropyl-β-D-thiogalactopyronoside (IPTG) was added to the medium and the cultivation was further continued for 5.5 hours. The culture liquid was centrifuged to obtain about 6 kg of wet cells which were frozen at −80° C.

(5) Activation of Met-NT-3

Forty grams of wet cells obtained in Reference Example 3(3) was suspended in 240 ml of 10 mM EDTA (pH 7.0). The cells in the suspension were destructed under ice cooling with supersonic waves using SONIFIER 450 (Branson Inc.), followed by centrifugation (10000 rpm, 1 hour). The resultant pellet was treated twice in the same manner as described above and washed. To the resultant pellet were added 160 ml of 50 mM Tris-HCl/4M urea/5 mM dithiothreitol (DTT) and the mixture was homogenized, followed by centrifugation. The resultant pellet was dissolved in 120 ml of 20 mM citric acid/8M urea (pH 3.0), followed by centrifugation to separate supernatant and precipitate. The precipitate was treated in the same manner as described above to obtain supernatant which was mixed with the above supernatant and 240 ml of pellet solution was obtained. The pellet solution was diluted with 760 ml of 100 mM acetate solution and passed through Sephadex G-25 column (11.3 cm φ×50 cm) equilibrated with 100 mM acetate solution to obtain 1640 ml of denatured Met-NT-3 solution from which urea was removed. This solution was allowed to stand at 4° C. for 2 days, to which 50 mM phosphate buffer/12.5% sucrose (pH 6.8) to obtain 8.5 L solution. The solution was adjusted to pH 6.0 using 5M sodium hydroxide or concentrated phosphoric acid and allowed to stand at 4° C. for 2 days to activate Met-NT-3. Thereafter, to the solution 200 mM copper sulfate was added to give a final concentration of 10 µM and the solution was stirred, followed by standing at 4° C. for 2 days to continue activation of Met-NT-3.

The solution obtained in Reference Example 3(5) was allowed to pass through SP-Sepharose Fast Flow column (2.5 cm φ×12 cm, Pharmacia Biotech Inc.) equilibrated with 100 mM phosphate buffer/0.1% 3-[(3-colamidepropyl) dimethylammonio]-1-propane sulfonate (CHAPS) (pH 6.0), followed by adsorption and washing with 100 mM phosphate buffer/0.1% CHAPS/200 mM sodium chloride (pH 6.0). The column was eluted with 100 mM phosphate buffer/0.1% CHAPS/400 mM sodium chloride (pH 6.0) to obtain solution containing Met-NT-3. The solution was boated on Resource 15 RPC column (2 cm φ×30 cm, Pharmacia Biotech Inc.), followed by elution using a linear concentration gradient consisting of 16% acetonitrile/0.1% TFA -36% acetonitrile/0.1% TFA. The eluted solution was subjected to freeze-drying to obtain about 28 mg of white powder of Met-NT-3.

Working Example 4

Fifty mg of Met-NT-3 obtained in Reference Example 3(6) was dissolved in 4.6 ml of water. To the mixture was added a solution containing 100 mM copper sulfate 200 µl, glyoxylic acid 92.5 mg and pyridine 200 µl, stirred gradually and allowed to stand at room temperature for 15 minutes. The reaction solution was passed through Sephadex G-25 column (2.5 cm φ×59 cm) equilibrated with 2M acetate buffer solution (pH 4.9) to collect 36 ml of diketone derivative of Met-NT-3. To this solution was added 78 mg o-phenylenediamine, and the reaction proceeded at 37° C. for 15 hours. The reaction solution was passed through Sephadex G-25 column (2.5 cm φ×59 cm) equilibrated with 2M acetate buffer solution (pH 4.9) to obtain the fraction of 76 ml NT-3. The obtained fraction was loaded on ODP-50 column, followed by eluting with a linear concentration gradient of (1) 0.1% TFA and (2) 0.1% TFA/80% acetonitrile to purify using HPLC and to obtain the fraction of NT-3. The obtained fraction was subjected to freeze-drying to obtain NT-3 powder.

Figure 2:
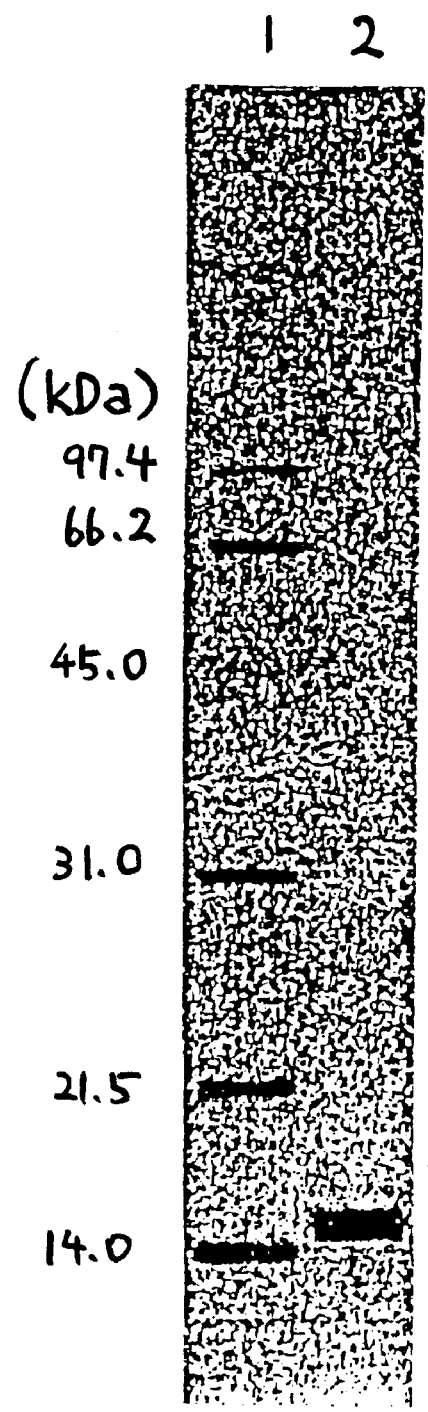
FIG. 2 shows the result of the electrophoresis obtained in Working Example 5a).

Working Example 5
(Determination of Feature of NT-3)
a) Analysis with SDS-polyacrylamide Gel Electrophoresis The powder of NT-3 obtained in Working Example 4 was suspended in Sample buffer [Laemmli, Nature, 227, 680 (1970)] and the mixture was heated with 100 mM DTT at 100° C. for 1 minute, followed by electrophoresis with Multi Gel 10/20 (Daiichi Kagaku Pure Chemicals). After electrophoresis, the gel was stained with Coomassie brilliant blue and only one single band of the purified protein was obtained. The result is shown in FIG. 2. In FIG. 2, Lanes 1–2 represent molecular weight markers and NT-3, respectively.

b) Analysis of N-terminal Amino Acid Sequence

The N-terminal amino acid sequence of NT-3 obtained in Working Example 4 was determined using a gas-phase protein sequencer (Applied Biosystems, 477A model). The N-terminal amino acid sequence of NT-3 obtained in Working Example 4 agreed with that predicted from cDNA sequence of NT-3. The results are shown in Table 4.

TABLE 4

Analysis of N-terminal amino acid sequence

| Residue No. | PTH[1])-amino acid detected | amino acid predicted from cDNA sequence of NT-3 |
|---|---|---|
| 1 | Tyr | Tyr |
| 2 | Ala | Ala |
| 3 | Glu | Glu |
| 4 | His | His |
| 5 | Lys | Lys |
| 6 | Ser | Ser |
| 7 | His | His |
| 8 | Arg | Arg |
| 9 | Gly | Gly |
| 10 | Glu | Glu |
| 11 | Tyr | Tyr |
| 12 | Ser | Ser |
| 13 | Val | Val |
| 14 | N.D. | Cys |
| 15 | Asp | Asp |
| 16 | Ser | Ser |
| 17 | Glu | Glu |
| 18 | Ser | Ser |
| 19 | Leu | Leu |
| 20 | Trp | Trp |

Analysis was carried out using 1 nmol of NT-3.
[1])phenylthiohydantoin

Analysis of Amino Acid Composition

About 20 μg of NT-3 obtained in Working Example 4 was used for the determination of amino acid composition with amino acid analyzer (Beckman 6300E ststem). The amino acid composition of NT-3 obtained in working Example 4 agreed with that predicted from cDNA sequence of NT-3. The results are shown in Table 5.

TABLE 5

Analysis of amino acid composition

| Amino acid | Number of residues per 1 mole | Values predicted from cDNA sequence of NT-3 |
|---|---|---|
| Asx | 11.3 | 11 |
| Thr[1]) | 9.4 | 9 |
| Ser[1]) | 12.8 | 12 |
| Glx | 12.1 | 11 |
| Pro | 2.1 | 2 |
| Gly | 7.9 | 8 |
| Ala | 4.7 | 5 |
| Cys[2]) | | 6 |
| Val | 8.7 | 9 |

TABLE 5-continued

Analysis of amino acid composition

| Amino acid | Number of residues per 1 mole | Values predicted from cDNA sequence of NT-3 |
|---|---|---|
| Met | 0 | 0 |
| Ile | 6.8 | 7 |
| Leu | 5.1 | 5 |
| Tyr | 4.9 | 5 |
| Phe | 1.1 | 1 |
| His | 3.7 | 4 |
| Lys | 10.0 | 10 |
| Arg | 10.2 | 10 |
| Trp[2]) | | 4 |

Acid hydrolysis (6N HCl, 1% phenol, 110° C., Mean value of those obtained after 24 and 48 hours of hydrolysis)
[1])Value extrapolated on the assumption that hydrolysis time was 0 hours.
[2])Undetected d) Analysis of C-terminal Amino Acid About 15 nmol of NT-3 obtained in Working Example 4 was used for the determination of C-terminal amino acid with amino acid analyzer (Beckman 6300E system). The C-terminal amino acid of NT-3 obtained in Working Example 4 agreed with that deduced from cDNA sequence of NT-3. The results are shown in Table 6.

TABLE 6

Analysis of C-terminal amino acid

| NT-3 | C-terminal amino acid | Yield (%) |
|---|---|---|
| | Thr | 51.1 |

Vapor-phase Hydrazinolysis (100° C., 3.5 hours)

Reference Example 4
Production of Met-human BTC

Met-human BTC was produced according to a method described in Examples 4–6, 8 and 13 of Japanese Patent Publication Laid-open No. 87894/1994.

(1) Construction of Human BTC cDNA Expression Plasmid of E. coli

A 0.6 kb EcoRI-BamHI fragment encoding mature human BTC (1–147 amino acid residues) was isolated from the plasmid pTB1515 described in Example 5 of Japanese Patent Publication Laid-open No. 87894/1994. After ligating synthetic adapters having ATG translational initiator codon (Sequence ID No.4: 5'TATGGATGGG 3; Sequence ID No.5: 5'AATTCCCATCCA3') to the EcoRI site of the above 0.6 kb fragment, the resulting 0.6 kb NdeI-BamHI fragment was inserted into the plasmid pET-3c carrying T7 promoter [Gene, 56. 125 (1987)] to construct the plasmid pTB1505.

To obtain a DNA fragment encoding the 80 amino acid residues of human BTC [1(Asp)-80 (Tyr) residues of FIGS. 10-1 to 10-2 of Japanese Patent Publication Laid-open No. 87894/1994], PCR was run using the plasmid pTB1505 as a template and 2 oligonucleotides (Sequence ID No.6: 5'ATA-CATATGGATGGGAATTCCA 3'; Sequence ID No.7: 5'CCGGATCCTAGTAAAACAAGTCAACTCT 3') as primers. The products were digested with NdeI and BamHI, fractionated by 2.0% agarose gel electrophoresis, and the expected 0.25 kb DNA fragment was isolated. This 0.25 kb BdeI-BamHI fragment was inserted downstream of the T7 promoter of pET-3c by ligating with T4 DNA ligase to give plasmid pTB1516 (cf. FIG. 13 of Japanese Patent Publication Laid-open No. 87894/1994).

(2) Expression of Human BTC in E. coli

Escherichia coli MM294 was lysogenized with lambda phage DE3 (Studier, supra), in which the RNA polymerase gene of T7 phage had been recombined. Thereafter, the plasmid pLysS was introduced into E. coli MM294(DE3) to give E. coli MM294(DE3)/pLysS. To this strain, plasmid pTB1516 obtained in Reference Example 4(1) was introduced, whereby E. coli MM294(DE3)/pLysS, pTB1516 was obtained. The transformant was cultivated in 20 ml of L-broth containing 100 µg/ml of ampicillin and 10 µg/ml of chloramphenicol at 37° C. When the Klett value was about 180, isopropyl beta-D-thiogalactoside (IPTG) was added to the medium to 0.4 mM as the final concentration, and the cultivation was continued for 4 hours. The bacterial cells were collected by centrifugation, and suspended in 0.5 ml of buffer containing 20 mM Tris-HCl (pH 7.4), 10 mM EDTA, 0.5M NaCl, 10% sucrose and 0.25 mM PMSF and then to the suspension egg white lysozyme was added at a concentration of 0.5 mg/ml. After keeping it in an ice-bath for one hour, the mixture was incubated at 37° C. for 5 minutes, and subjected to centrifugation (SORVALL, 15000 rpm for 30 minutes at 4° C.) to give a supernatant.

The transformant Escherichia coli MM294(DE3)/pLysS, pTB1516 has been deposited at the IFO on Apr. 16, 1992 under the deposition number of IFO 15282, as well as in the Fermentation Research Institute, Agency of Industrial Science and Technology, Ministry of International Trade and Industry, Japan (FRI) on Apr. 21, 1992 under Accession No. FERN BP-3836.

(3) Purification of BTC Produced by a E. coli Transformant

The transformant E. coli MM294 (DE3)/pLysS, pTB1516 obtained in Reference Example 4(2) was cultured for one night and the culture was transferred into a LB medium and the medium was cultivated at 37° C. for 2 hours. IPTG was added to the system to a final concentration of 0.1 mM and the cultivation was continued for 3 hours. The cells were collected by centrifugation and stored at −20° C.

The stored cells in the amount of 5 liters were thawed and it was suspended in a 300 ml of buffer containing 50 mM Tris-HCl (pH 7.4), 10 mM EDTA, 0.2 M NaCl, 10% sucrose and 1 mM APMSF. To the suspension, 40 mg of egg white lysozyme was dissolved, and the solution was incubated at 4° C. for 2 hours and subjected to ultrasonic treatment and then centrifugation at 20000×g for 1 hour to give a supernatant. The supernatant was passed through 200 ml of Q-Sepharose bed, and TCA was added to the resultant product to obtain a final concentration of 4% and allowed to stand still for 10 minutes at 4° C. A precipitate was collected by centrifugation for 20 minutes at 20000×g, and suspended in a buffer containing 100 ml of 20 mM Tris (pH 7.4), 1 mM EDTA and 1 mM APMSF, and to the resultant composition 5N NaOH was added to adjust pH to 6, while homogenizing in a mortar. This homogenate was subjected to centrifugation at 100000×g for 1 hour, and the resulting supernatant was applied to S-Sepharose column (diameter 1.6×10 cm: Pharmacia). After washing a column with a buffer containing 0.1M potassium phosphate (pH 6), 1 mM EDTA and 1 mM APMSF, a gradient elution was carried out with 400 ml of 0M to 1M of NaCl for 200 minutes. Each 5 mol of the eluates were collected. Highly active fractions Nos. 20 to 27 were pooled as E. coli BTC.

To the pooled fraction TFA was added to obtain a final concentration of 0.1% and then the mixture was applied to C18 reverse phase HPLC column (Asahipak ODP-50, diameter 1.0×25 cm, Asahi Chemical Industries Co., Ltd.). After washing the column with 0.1% TFA, the eluate thus obtained was applied to a gradient elution of 340 ml of acetonitrile (0–63%) for 170 minutes. The procedure gave 630 µg of E. coli BTC.

N-teminal amino acid sequence of E. coli BTC were determined up to 20 amino acids. The sequence of BTC has Met derived from initiation condon at its N-terminal as expected.

Working Example 6

Twenty mg of human betacellulin having methionine at its N-terminal (Met-BTC) obtained in Reference Example 4(3) was dissolved in 16 ml of 50 mM phosphate buffer solution (pH 8.0). To the mixture was added a solution containing 0.1M copper sulfate 2 ml, glyoxylic acid 0.92 g and pyridine 2 ml and allowed to stand at 25° C. for 1 hour. The reaction solution was passed through Sephadex G-25 column (25 mmID×600 mmL) equilibrated with 2M acetate-2M sodium acetate buffer solution and the column washed with the same buffer solution at 6 ml/minute of flow rate to collect the fraction of diketone derivative of Met-BTC. To this fraction was added o-phenylenediamine to give a final concentration of 20 mM, followed by vacuum and sealing with nitrogen gas, and the reaction was proceeded at 37° C. for 20 hours. The reaction solution was passed through Sephadex G-25 column (25 mmID×600 mmL) equilibrated with 20 mM Tris buffer solution (pH 8.0) and the column was washed with the same buffer solution at 6 ml/minute of flow rate to collect the fraction of human betacellulin having no methionine at its N-terminal (BTC). The collected fraction was adjusted to pH 6.0 and loaded on SP-Sepharose column (10 mmID×200 mmL) equilibrated with 100 mM phosphate buffer solution (pH 6.0), followed by eluting with a linear concentration gradient of 0–100% solution B (B=100 mM phosphate buffer solution +1M sodium chloride, pH 6.0) at 2.0 ml/minute of flow rate for 60 minutes to collect the fraction of BTC. The collected fraction was passed through ODP-50 column (10 mmID×250 mmL) (Showa Denko, Inc.) equilibirated with 0.1% TFA, followed by eluting with a linear concentration gradient of 20–40% solution B (B=acetonitrile/0.1% TFA) at 2 ml/minute of flow rate for 40 minutes to collect the fraction of BTC. The collected fraction was subjected to freeze-drying to obtain BTC powder.

Working Example 7

(Determination of Feature of BTC)

a) Analysis with SDS-polyacrylamide Gel Electrophoresis

Figure 3:
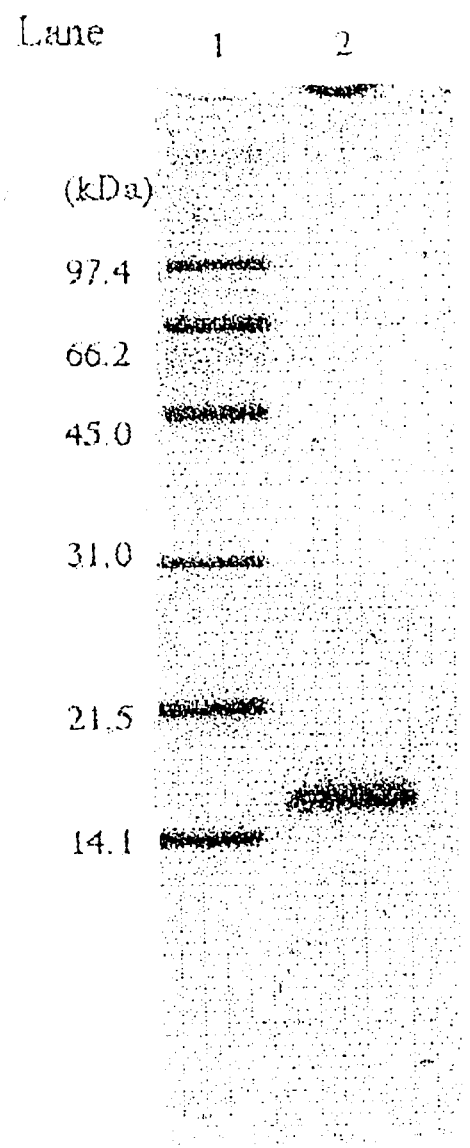
FIG. 3 shows the result of the electrophoresis obtained in Working Example 7a).

The powder of BTC 1 µg obtained in Working Example 6 was suspended in Sample buffer [Laemmli, Nature, 227, 680 (1970)] and the mixture was heated with 100 mM DTT at 100° C. for 1 minute, followed by electrophoresis with Multi Gel 15/25 (Daiichi Pure Chemicals). After electrophoresis, the gel was stained with Coomassie brilliant blue and only one single band of the purified protein was obtained. The result is shown in FIG. 3. In FIG. 3, Lanes 1–2 represent molecular weight markers and BTC, respectively.

b) Analysis of N-terminal Amino Acid Sequence

The N-terminal amino acid sequence of BTC 1 nmol obtained in Working Example 6 was determined using a gas-phase protein sequencer (Applied Biosystems, 477A model). The N-terminal amino acid sequence of BTC obtained in Working Example 6 agreed with that predicted from cDNA sequence of BTC. The results are shown in Table 7.

TABLE 7

Analysis of N-terminal amino acid sequence

| Residue No. | PTH[1])-amino acid detected | amino acid predicted from cDNA sequence of BTC |
|---|---|---|
| 1 | Asp | Asp |
| 2 | Gly | Gly |
| 3 | Asn | Asn |
| 4 | Ser | Ser |
| 5 | Thr | Thr |
| 6 | Arg | Arg |
| 7 | Ser | Ser |
| 8 | Pro | Pro |
| 9 | Glu | Glu |
| 10 | Thr | Thr |
| 11 | Asn | Asn |
| 12 | Gly | Gly |
| 13 | Leu | Leu |
| 14 | Leu | Leu |
| 15 | N.D. | N.D. |
| 16 | Gly | Gly |
| 17 | Asp | Asp |
| 18 | Pro | Pro |
| 19 | Glu | Glu |
| 20 | Glu | Glu |

[1])phenylthiohydantoin c) Analysis of Amino Acid Composition

About 20 μg of BTC obtained in Working Example 6 was used for the determination of amino acid composition with amino acid analyzer (Beckman 6300E system). The amino acid composition of BTC obtained in Working Example 6 agreed with that predicted from cDNA sequence of BTC. The results are shown in Table 8.

TABLE 8

Analysis of amino acid composition

| Amino Acid | Number of residues per 1 mole | Values predicted from cDNA sequence of BTC |
|---|---|---|
| Asx | 7.0 | 7 |
| Thr[1]) | 5.9 | 6 |
| Ser[1]) | 4.8 | 5 |
| Glx | 9.7 | 9 |
| Pro | 4.0 | 4 |
| Gly | 7.0 | 7 |
| Ala | 4.0 | 4 |
| Cys[2]) | N.D. | 8 |
| Val | 3.6 | 4 |
| Met | 0 | 0 |
| Ile | 2.0 | 2 |
| Leu | 3.0 | 3 |
| Tyr | 3.8 | 4 |
| Phe | 3.0 | 3 |
| His | 2.1 | 2 |
| Lys | 5.1 | 5 |
| Arg | 6.4 | 7 |
| Trp[2]) | | 0 |

Acid hydrolysis (6N HCl, 1% phenol, 110° C., Mean value of those obtained after 24 and 48 hours of hydrolysis)
[1])Value extrapolated on the assumption that hydrolysis time was 0 hours.
[2])Undetected d) Analysis of C-terminal Amino Acid About 15 nmol of BTC obtained in Working Example 6 was used for the determination of C-terminal amino acid with amino acid analyzer (Beckman 6300E system). The C-terminal amino acid of BTC obtained in Working Example 6 agreed with that predicted from cDNA sequence of BTC. The results are shown in Table 9.

TABLE 9

Analysis of C-terminal amino acid

| BTC | C-terminal amino acid | Yield (%) |
|---|---|---|
| | Thr | 65.5 |

Vapor-phase Hydrazinolysis (100° C., 3.5 hours)

e) Determination of BTC Biological Activity

Assay of BTC purified and obtained in Working Example 6 was carried out using BALB/C3T3 A31-714 clone 4 (International Journal of Cancer, 12, 463 (1973)) according to the method described in Molecular Cell Biology, 8, 588 (1988) and revealed that BTC purified and obtained in Working Example 6 had an activity almost similar to a standard product.

Reference Example 5

Production of Methionyl Human Interleukin-2:

Met-IL-2 was produced according to a method described in Reference Example 2 of Japanese Patent Publication Laid-open No. 171699/1987.

(i) Construction of Expression Plasmid:

A 1294bp DNA fragment was cleaved from a human IL-2 gene-containing plasmid pILOT 135-8 (Refer to Example 1(vii) of Japanese Patent Publication Laid-open No. 11528/1985] with restriction enzyme HgiAI. The cleaved 1294bp DNA fragment was treated with T4 DNA polymerase to have flat ends and was linked with an EcoRI linker dTGC-CATGAATTCATGGCA (Sequence ID No.8) using T4 DNA ligase. The resulting DNA was digested with EcoRI, yielding a DNA fragment having translation initiation codon ATG and a human IL-2 gene.

Using T4 DNA ligase, the resulting DNA fragment was inserted into plasmid ptrp781 [Nucleic Acids REsearch, 11, 3077 (1983)], the EcoRI-PstI site of which had been digested. The resulting expression plasmid pTF1 has both a translation initiation codon and a human IL-2 gene downstream from trp promotor (FIG. 4 of Japanese Patent Publication Laid-open No. 171699/1987).

Using restriction enzyme StuI, a DNA fragment was cleaved from the pTF1 plasmid and then linked with a BamHI linker. The resulting plasmid DNA was treated with restriction enzymes BamHI and EcoRI, followed by insertion into a plasmid pTB281, which has λPL promotor as its EcoRI-BamHI site. The resulting expression plasmid was named pTB285 (FIG. 5 of Japanese Patent Publication Laid-open No. 171699/1987).

(ii) Production of Transformant

Using the pTB285 plasmid obtained above, *Escherichia coli* N4830 was transformed in accordance with the method of Cohen et al. [Proceedings of the National Academy of Sciences, USA, 69, 2110 (1972)], yielding a transformant having plasmid pTB285; the transformant was named *Escherichia coli* N4830/pTB285.

(iii) Cultivation of the Transformant:

A transformant *Escherichia coli* N4830/pTB285 (IFO 14437, FERM BP-852) was inoculated into a 250 ml flask containing 50 ml of a liquid medium (pH 7.0) containing 1% Bacto TRYPTONE (Difco Laboratories, USA), 0.5% Bacto YEAST EXTRACT (Difco Laboratories, USA), 0.5% sodium chloride and 50 μg/ml ampicillin, and then subjected to rotary shaking cultivation at 37° C. over night. The resulting culture liquid was then transferred to a 5 l jar fermentor containing 2.5 l of M9 medium containing 0.5% Casamino acid, 0.5% glucose and 50 μg/ml ampicillin, after which it was subjected to cultivation under aeration and agitation at 35° C. for 6 hours and 42° C. for 3 hours, yielding 2.5 l of culture liquid which was then centrifuged to harvest bacterial cells. The cells were frozen at −80° C. and stored.

(iv) Extraction:

Twenty grams of the frozen cell sample was uniformly suspended in 100 ml of an extraction solvent (pH 7.0) containing 7M guanidine hydrochloride and 0.1M Tris-HCl, and stirred at 4° C. for 1 hour. The resulting suspension was then centrifuged at 28,000×g for 20 minutes, yielding a supernatant.

(v) Partial Purification of Methionyl Interleukin-2 Protein

The resulting supernatant, after dialyzation against a 0.01M Tris-HCl buffer solution (pH 8.5), was centrifuged at 19,000×g for 10 minutes, again yielding a supernatant. The resulting supernatant was passed through a 50 ml column packed with DE52 (DEAE cellulose, Wattman, UK) equilibrated with a 0.01M Tris-HCl buffer (pH 8.5) to adsorb protein; IL-2 was then eluted using a NaCl concentration linear gradient (0.15M NaCl, 1 l), yielding an active fraction.

(vi) Purification of Methionyl Interleukin-2 Protein:

After being concentrated to 5 ml using a YM-5 menbrane (Amicon, USA), the active fraction obtained above was subjected to gel filtration using a column (500 ml capacity) packed with Sephacryl S-200 (Pharmacia, Sweden) previously equilibrated with a 0.1M Tris-HCl (pH 8.0)-1M NaCl buffer. Forty milliliters of the resulting active fraction was concentrated to 3 ml using a YM-5 membrane. The resulting concentrate was adsorbed in an Ultrapore RPSC column (Altex, USA) and subjected to HPLC using a trifluoroacetic acid-acetonitrile system as eluent. The following conditions were maintained.

Column: Ultrapore RPSC (4.6×75 mm)
Column temperature: 30° C.
Elution solvent A: 0.1% trifluoroacetic acid-99.9% water
Elution solvent B: 0.1% trifluoroacetic-99.9% acetonitrile
Elution program: 0 min. (68% A+32% B)–25 min. (55% A+45% B)–35 min. (45% A+55% B)–45 min. (30% A+70% B)–48 min. (100% B)
Flow rate: 0.8 ml/min.
Detection wavelength: 230 nm The fraction of Met-IL-2 was collected at approx. 39 min. of retention time.

(vii) Purification of Met-IL-2 Using SP-5PW Column:

0.5 ml of a 0.005M ammonium acetate buffer containing the mixture obtained above (pH 5.0, protein concentration 1.03 mg/ml) was adsorbed on an SP-5PW column for HPLC (0.75×7.5 cm, Tosoh) equilibrated with a 0.025M phosphate buffer solution (pH 7.4) to elute protein. Column temperature and flow rate were maintained at 35° C. and 0.5 ml/min. respectively. A varian 5,500 model liquid chromatograph was used.

The fraction of Met-IL-2 was collected at approx. 70 min. of retension time.

Working Example 8

Twenty mg of methionyl human interleukin-2 (Met-IL-2) obtained in Reference Example 5 was dissolved in 27 ml of 20 mM ammonium acetate buffer solution (pH 5.0). To the mixture was added a solution containing 25 mM copper sulfate 3.375 ml, glyoxylic acid 1.55 g and pyridine 3.375 ml and allowed to stand at room temperature for 1 hour. The reaction solution was passed at 300 ml/hour of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was passed at 300 ml/hour of flow rate through Sephadex G-25 column (25 mmID×600 mmL) equilibrated with 20 mM ammonium acetate buffer solution (pH 5.0) to collect the fraction of human interleukin-2 (IL-2). The collected IL-2 fraction was loaded on a SP-5PW column equilibrated with 25 mM phosphate buffer solution (pH 7.0), followed by eluting with a pH gradient of 30–80% solution B (B=25 mM phosphate, pH 8.0) at 1.0 ml/minute of flow rate for 25 minutes to collect the fraction of IL-2. The collected fraction was passed through ODP-50 column (4.6 mmID×150 mmL) equilibrated with (1) 0.1% TFA and (2) 0.1% TFA+80% acetonitrile (80%:20%), followed by eluting with a linear concentration gradient of 20–100% solution B at 0.8 ml/minute of flow rate for 15 minutes to collect the fraction of IL-2. The collected fraction was subjected to freeze-drying to obtain a freeze-dried IL-2 powder.

Working Example 9
(Determination of Feature of IL-2)

a) Analysis with SDS-polyacrylamide Gel Electrophoresis

Figure 4:
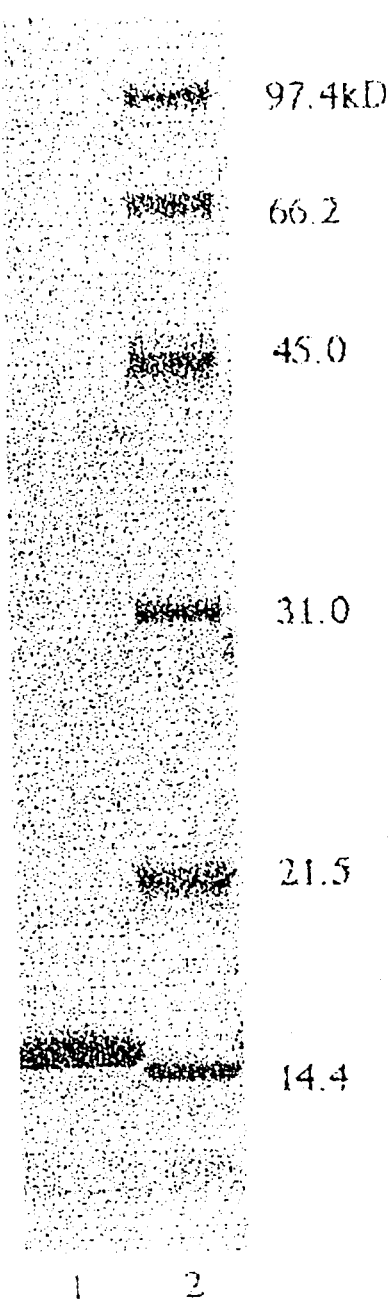
FIG. 4 shows the result of the electrophoresis obtained in Working Example 9a).

The powder of IL-2 3 µg obtained in Working Example 8 was suspended in Sample buffer [Laemmli, Nature, 227, 680 (1970)] and the mixture was heated with 100 mM DTT at 100° C. for 5 minutes, followed by electrophoresis with Multi Gel 10/20 (Daiichi Pure Chemicals). After electrophoresis, the gel was stained with Coomassie brilliant blue and only one single band of the purified protein was obtained. The result is shown in FIG. 4. In FIG. 4, Lanes 1–2 represent IL-2 and molecular weight markers, respectively.

b) Analysis of N-terminal Amino Acid Sequence

The N-terminal amino acid sequence of Il-2 1 nmol obtained in Working Example 8 was determined using a gas-phase protein sequencer (Applied Biosystems, 477A model). The N-terminal amino acid sequence of IL-2 obtained in Working Example 8 agreed with that predicted from cDNA sequence of IL-2. The results are in Table 10.

TABLE 10

| | Analysis of N-terminal amino acid sequence | |
|---|---|---|
| Residue No. | PTH[1]-amino acid detected | amino acid predicted from cDNA sequence of IL-2 |
| 1 | Ala | Ala |
| 2 | Pro | Pro |
| 3 | Thr | Thr |
| 4 | Ser | Ser |
| 5 | Ser | Ser |
| 6 | Ser | Ser |
| 7 | Thr | Thr |
| 8 | Lys | Lys |
| 9 | Lys | Lys |
| 10 | Thr | Thr |
| 11 | Gln | Gln |
| 12 | Leu | Leu |
| 13 | Gln | Gln |
| 14 | Leu | Leu |
| 15 | Glu | Glu |
| 16 | His | His |
| 17 | Leu | Leu |
| 18 | Leu | Leu |
| 19 | Leu | Leu |
| 20 | Asp | Asp |

[1]phenylthiohydantoin c) Analysis of Amino Acid Composition

About 20 µg of IL-2 obtained in Working Example 8 was used for the determination of amino acid composition with amino acid analyzer (Beckman 6300E system). The amino acid composition of IL-2 obtained in Working Example 8 agreed with that predicted from cDNA sequence of IL-2. The results are shown in Table 11.

TABLE 11

Analysis of amino acid composition

| Amino Acid | Number of residues per 1 mole | Values predicted from cDNA sequence of IL-2 |
|---|---|---|
| Asx | 12.0 | 12 |
| Thr[1)] | 12.9 | 13 |
| Ser[1)] | 8.0 | 8 |
| Glx | 18.5 | 18 |
| Pro | 5.0 | 5 |
| Gly | 2.1 | 2 |
| Ala | 5.0 | 5 |
| Cys | — | 3 |
| Val | 3.5 | 4 |
| Met | 4.0 | 4 |
| Ile | 9.1 | 9 |
| Leu | 22.4 | 22 |
| Tyr | 3.0 | 3 |
| Phe | 6.0 | 6 |
| His | 3.1 | 3 |
| Lys | 11.0 | 11 |
| Arg | 4.1 | 4 |
| Trp | — | 1 |

Acid hydrolysis (6N HCl, 1% phenol, 110° C., Mean value of those obtained after 24 and 48 hours of hydrolysis)
[1)]Value extrapolated on the assumption that hydrolysis time was 0 hours.
—: Undetected d) Analysis of C-terminal Amino Acid About 15 nmol of IL-2 obtained in Working Example 8 was used for the determination of C-terminal amino acid with an amino acid analyzer (Beckman 6300E system). The C-terminal amino acid of IL-2 obtained in Working Example 8 agreed with that predicted from cDNA sequence of IL-2. The results are shown in Table 12.

TABLE 12

Analysis of C-terminal amino acid

| IL-2 | C-terminal amino acid | Yield (%) |
|---|---|---|
| | Thr | 30.0 |

Vapor-phase Hydrazolysis (100° C., 3.5 hours)

e) Determination of IL-2 Biological Activity

An assay of IL-2 purified and obtained in Working Example 8 was carried out using interleukin-2 dependent cells according to the method described in Biochem. Biophys. Res. Commun., 109, 363 (1982) and revealed that IL-2 purified and obtained in Working Example 8 had an activity almost similar to a standard product.

According to the method of the present invention, a N-terminal methionine residue can be removed selectively, specifically and efficiently from a peptide (including a protein) or a salt thereof having the methinine residue at its N-terminal. According to the method of the present invention, irrespective of species of the peptide, N-terminal methionine residue can be chemically removed under mild conditions. Therefore, the method of the present invention is useful for industrial production of a peptide having a natural type amino acid sequence from the material peptide produced by gene recombination technology, i.e., having any N-terminal methionine residue to be removed.

Reference Example 6
(Construction of expression vector for human growth hormone (hGH) using T7 promoter)

The structure gene of hGH was isolated as about 0.75 kb of EcoRI-EcoRV fragment from plasmid pHGH107 (ATCC 31538 or ATCC 40011) described in Japanese Patent Publication Number 12996/1994. On the other hand, T7 promoter and ampicillin resistant gene were isolated as about 4.6 kb of NdeI-BamHI fragment from pET-3C [Rosenberg et al., Gene, 56, 125 (1987)]. Both of the two fragments were treated with T4 DNA polymerase (DNA blunting kit; Takara Shuzo, Inc.) and ligated with T4 DNA ligase, followed by introduction into Escherichia coli JM109 and selection of ampicillin resistant transformant. From the obtained 12 colonies, plasmids were prepared and digested with PstI. As a result, it was found that hGH gene was inserted in a correct direction in the plasmids from the 6 colonies. The plasmid obtained from one transformant among the 6 colonies was named as pTGA201.

Reference Example 7
(Expression of Met-hGH in Escherichia coli)

Escherichia coli JM109 was transformed with λ phage (Studie, Supura) having RNA polymerase gene of T7 phage. Thereafter, into the obtained Escherichia coli JM109 (DE3), hGH expression vector pTGA201 obtained in Reference Example 6 was introduced to obtain Escherichia coli JM109 (DE3)/pTGA201 [FERM BP-5632; IFO 16001].

Escherichia coli JM109 (DE3)/pTGA201 was inoculated into a 2 liter capacity of flask containing 1 liter of LB medium [1% peptone, 0.5% yeast extract, 0.5% sodium chloride] comprising 50 μg/ml ampicillin and then subjected to rotary shaking cultivation at 30° C. for 16 hours. The resultant culture liquid was then transferred to a 50 liter jar fermentor containing 20 liter of LB medium [0.02% antifoaming agent (New Pole LB-625; San-yo Kasei Kogyo), 50 μg/ml ampicillin], after which it was subjected to cultivation under aeration and agitation at 37° C. for 6 hours. The resultant culture liquid was then transferred to a 500 liter jar fermentor containing 360 liter of a liquid production medium [1.68% sodium hydrogen phosphate, 0.3% potassium dihydrogen phosphate, 0.1% ammonium chloride, 0.05% sodium chloride, 0.024% magnesium sulfate, 0.02% antifoaming agent (New Pole LB-625), 0.0005% thiamine hydrochloride, 1.5% glucose, 1.5% casamino acid], after which it was subjected to cultivation under aeration and agitation at 37° C. When the Klett value was about 500, 5.95 mg/L/minute of isopropyl-β-D-thiogalactopyronoside (IPTG) was added to the medium and the cultivation was further continued for 4 hours. The culture liquid was centrifuged to obtain about 4.5 kg of wet cells which were frozen at −80° C.

Reference Example 8
(Activation of Met-hGH)

Two kg of wet cells obtained in Reference Example 7 was dissolved in 6 l of 50 mM Tris-HCl and guanidine hydrochloride (pH 8.0), followed by centrifugation (10000 rpm, 120 minutes). To 6 l of the resultant supernatant, was added 18 l of a solution (pH 8.0) containing 50 mM Tris-HCl, 0.28 mM GSSG and 0.7 M Arg to adjust pH 8. 0, followed by standing at 4° C. for 5 days to continue activation of Met-hGH.

Reference Example 9
(Purification of Met-hGH)

The solution obtained in Reference Example 8 was subjected to salting-out and concentration by Pellicon cassette system (PTGC membrane; Millipore Corporation) with adding a solution (pH 8.0) of 20 mM Tris-HCl and 2.5 M urea until electric conduction became not more than 10 mS. The obtained concentrate was centrifuged (10000 rpm, 60 minutes) to obtain 5 l of supernatant. The supernatant was loaded on DEAE-Toyopearl 650M column (20 cm φ×84 cm, Tosoh) equilibrated with a solution (pH 8.0) of 20 mM Tris-HCl and 2.5 M urea, followed by adsorption and washing. The column was eluted with using a linear concentration gradient consisting of 0–25% solution B (B=20 mM Tris-HCl, 2.5 M urea, 1M NaCl, pH 8.0) at 300 ml/minute of flow rate for 100 minutes. The eluted solution 10 l containing Met-hGH was again subjected to salting-out and concentration by Pellicon cassette system (PTGC membrane; Millipore). The concentrated solution was passed through DEAE-5PW column (21 cm φ×30 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 320 ml/minute of flow rate for 70 minutes. To the obtained Met-hGH fraction 6 l, was added 2 M Tris-HCl (pH 7.8) to adjust pH 7.2, followed by salting-out and concentration by Pellicon cassette system (PTGC membrane; Millipore) to obtain 9,979 mg of Met-hGH.

Working Example 10

(Removal of N-terminal Met)

To 1650 ml solution of Met-hGH obtained in Reference Example 9, was added 413 ml solution containing 35 mM copper sulfate, 2.5 M glyoxylic acid and 6 M pyridine and the mixture was stirred and allowed to stand at 25° C. for 1 hour. The reaction solution was passed at 3 l/h of flow rate through Sephadex G-25 column (11.3 cm φ×125 cm, Pharmacia) equilibrated with a solution (pH 8.0) of 20 mM Tris-HCl and 2.5 M urea and the column washed with the same solution to collect the fraction of diketone derivative of Met-hGH. The eluted fraction was directly added to 4 l solution of 4M acetic acid, 4 M sodium acetate, 80 mM o-phenylenediamine and 3 M urea with stirring. After the elution, the reaction solution 8 l was allowed to stand at 4° C. for 3 days. The solution was subjected to salting-out by Pellicon cassette system (PTGC membrane; Millipore). The concentrated solution 4 l was passed at 3 l/h of flow rate through Sephadex G-25 column (11.3 cm φ×140 cm, Pharmacia) equilibrated with a solution (pH 8.0) of 20 mM Tris-HCl and 2.5 M urea to collect the fraction 4.7 l of hGH. The obtained fraction was passed through DEAE-5PW column (21 cm φ×30 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 320 ml/minute of flow rate for 70 minutes to collect 10 l fraction of hGH. To the obtained hGH fraction, was added 500 ml solution of 2 M Tris-HCl (pH 7.8) to adjust pH 7.2, followed by concentration with Minitan II (PTGC membrane; Millipore). The concentrated solution 500 ml was passed at 2 l/h of flow rate through Sephacryl S-100 column (11.3 cm φ×50 cm, Pharmacia) equilibrated with distilled water to collect the hGH fraction 1651 ml, followed by filtration with Millipack 60 (Millipore) to obtain hGH solution 1487 ml (3309 mg of hGH).

Working Example 11

(Determination of Feature of hGH)

a) Analysis with SDS-polyacrylamide Gel Electrophoresis

Figure 5:
FIG. 5 shows the result of the electrophoresis obtained in Working Example 11a).

To the hGH solution obtained in Working Example 10 was added the same volume of Sample buffer [Laemmli, Nature, 227, 680 (1970)] containing 100 mM DTT, and the mixture was heated at 95° C. for 2 minutes, followed by electrophoresis with Multi Gel 10/20 (Daiichi Pure Chemicals). After electrophoresis, the gel was stained with Coomassie brilliant blue and only one single band at about 22 kd of the purified protein was obtained. The result is shown in FIG. 5. In FIG. 5, Lanes 1–2 represent molecular weight markers and hGH, respectively.

b) Analysis of N-terminal Amino Acid Sequence

The N-terminal amino acid sequence of hGH obtained in Working Example 10 was determined using a gas-phase protein sequencer (Applied Biosystems, 477A model). The N-terminal amino acid sequence of hGH obtained in Working Example 10 agreed with that predicted from cDNA sequence of hGH. The results are shown in Table 13.

TABLE 13

Analysis of N-terminal amino acid sequence

| | PTH[1]-amino acid | | amino acid predicted from |
|---|---|---|---|
| Residue No. | detected | (pmol) | cDNA sequence of hGH |
| 1 | Phe | (949) | Phe |
| 2 | Pro | (404) | Pro |
| 3 | Thr | (422) | Thr |
| 4 | Ile | (744) | Ile |
| 5 | Pro | (283) | Pro |
| 6 | Leu | (514) | Leu |
| 7 | Ser | (136) | Ser |
| 8 | Arg | (36) | Arg |
| 9 | Leu | (377) | Leu |
| 10 | Phe | (408) | Phe |
| 11 | Asp | (77) | Asp |
| 12 | Asn | (230) | Asn |
| 13 | Ala | (435) | Ala |
| 14 | Met | (334) | Met |
| 15 | Leu | (398) | Leu |
| 16 | Arg | (67) | Arg |
| 17 | Ala | (488) | Ala |
| 18 | His | (30) | His |
| 19 | Arg | (42) | Arg |
| 20 | Leu | (406) | Leu |

Analysis was carried out using 1 nmol of hGH.
[1]phenylthiohydantoin c) Analysis of amino acid composition About 20 μg of hGH obtained in Working Example 10 was used for the determination of amino acid composition with amino acid analyzer (L-8500A, Hitachi). The amino acid composition of hGH obtained in Working Example 10 agreed with that predicted from cDNA sequence of hGH. The results are shown in Table 14.

TABLE 14

Analysis of amino acid composition

| Amino acid | Number of residues per 1 mole | Values predicted from cDNA sequence of hGH |
|---|---|---|
| Asx | 20.2 | 20 |
| Thr[1] | 10.0 | 10 |
| Ser[1] | 16.7 | 18 |
| Glx | 27.0 | 27 |
| Pro | 8.1 | 8 |
| Gly | 8.2 | 8 |
| Ala | 7.6 | 7 |

TABLE 14-continued

Analysis of amino acid composition

| Amino acid | Number of residues per 1 mole | Values predicted from cDNA sequence of hGH |
|---|---|---|
| Cys[2)] | N.D. | 4 |
| Val | 7.0 | 7 |
| Met | 3.0 | 3 |
| Ile | 7.7 | 8 |
| Leu | 27.9 | 26 |
| Tyr | 8.1 | 8 |
| Phe | 12.7 | 13 |
| His | 3.2 | 3 |
| Lys | 8.9 | 9 |
| Arg | 10.9 | 11 |
| Trp | 0.8 | 1 |

Acid hydrolysis (6N HCl, 4% thioglycolic acid, 110° C., Mean value of those obtained after 24 and 48 hours of hydrolysis)
[1)]Value extrapolated on the assumption that hydrolysis time was 0 hours.
[2)]Undetected d) Analysis of C-terminal Amino Acid About 15 nmol of hGH obtained in Working Example 10 was used for the determination of C-terminal amino acid with amino acid analyzer (L-8500A, Hitachi). The C-terminal amino acid of hGH obtained in Working Example 10 agreed with that predicted from cDNA sequence of hGH. The results are shown in Table 15.

TABLE 15

Analysis of C-terminal amino acid

| C-terminal amino acid | Yield (%) |
|---|---|
| Phe | 52 |

Vapor-phase Hydrazinolysis (100° C., 3.5 hours)

Working Example 12
(Determination of rhGH activity)

Assay of hGH purified and obtained in Working Example 10 was carried out using Nb 2 cells according to the method described in Journal of Clinical Endocrinology and Metabolism, 51, 1058 (1980) and revealed that hGH purified and obtained in Working Example 10 had a cell growth enhancing activity almost similar to a standard product (Chemicon International, USA).

Working Example 13
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM nickel chloride and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM o-phenylenediamine and the mixture was stirred and allowed to stand at 37° C. for 15 hours. The reaction solution was passed through Sephadex G-25 column (10 mmID× 40cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 14
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM cobalt chloride and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM o-phenylenediamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 15
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0. 4 M glyoxylic acid, 20 mM zinc sulfate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM o-phenylenediamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-

Working Example 16
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM copper acetate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM o-phenylenediamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 17
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM copper sulfate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM tolylene-3,4-diamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 18
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM copper sulfate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM 4-chloro-o-phenylenediamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 19
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM copper sulfate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM 3,4-diaminobenzoic acid and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 20
(Removal of N-terminal Met)

The solution of Met-hGH obtained in Reference Example 9 was substituted with a solution (pH 8.0) of 20 mM Tris-HCl and 8 M urea and concentrated to a solution of 10 mg/ml Met-hGH, using ultrafiltration system (Diaflo membrane YM 10, 43 mm; Amicon). To the obtained solution 1 ml, was added 1 ml solution (pH 7.0) containing 4 M sodium acetate, 20 mM acetic acid, 0.4 M glyoxylic acid, 20 mM copper sulfate and 6 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 4 M urea to collect the fraction of diketone derivative of Met-hGH. To the eluted solution was added the same volume of a solution containing 4M acetic acid, 4 M sodium acetate and 80 mM cysteamine and the mixture was stirred and allowed to stand at 37° C. for 15 hours. The reaction solution was passed through Sephadex G-25 column (10 mmID×40 cmL, Pharmacia) equilibrated with a solution (pH 8.0) of 20 mM Tris-HCl to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 21
(Removal of N-terminal Met)

The solution of Met-hGH obtained in Reference Example 9 was substituted with a solution (pH 8.0) of 20 mM Tris-HCl and 3 M urea and concentrated to a solution of 5 mg/ml Met-hGH, using ultrafiltration system (Diaflo membrane YM 10, 43 mm; Amicon). To the obtained solution 2 ml, was added 2 ml solution containing 4 M sodium acetate, 0.8 mM acetic acid, 0.4 M glyoxylic acid, 10 mM copper sulfate and 2.5 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 2.5 M urea to collect the fraction of diketone derivative of Met-hGH. To the eluted solution was added the same volume of a solution containing 4 M acetic acid, 4 M sodium acetate, 3 M urea and 80 mM o-phenylenediamine and the mixture was stirred and allowed to stand at 4° C. for 3 days. The reaction solution was passed through Sephadex G-25 column (10 mmID×40 cmL, Pharmacia) equilibrated with a solution (pH 8.0) of 20 mM Tris-HCl and 2.5 M urea to collect the fraction of hGH. The obtained fraction was passed through DEAE-5PW column (2.15 cm φ×15 cm, Tosoh) using HPLC method (Gilson HPLC system; Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 22
(Removal of N-terminal Met)

The solution of Met-hGH obtained in Reference Example 9 was substituted with a solution (pH 8.0) of 20 mM Tris-HCl and 3 M urea and concentrated to a solution of 5 mg/ml Met-hGH, using ultrafiltration system (Diaflo membrane YM 10, 43 mm; Amicon). To the obtained solution 2 ml, was added 2 ml solution containing 1 M imidazole, 0.5 M glyoxylic acid, 20 mM copper sulfate and 2.5 M urea and the mixture was stirred and allowed to stand at room temperature for 60 minutes. The reaction solution was passed through Sephadex G-25 column (10 mmID×30 cmL, Pharmacia) equilibrated with a solution (pH 8.0) of 20 mM Tris-HCl and 2.5 M urea to collect the fraction of diketone derivative of Met-hGH. To the eluted solution was added the same volume of a solution containing 4 M acetic acid, 4 M sodium acetate, 3 M urea and 80 mM o-phenylenediamine and the mixture was stirred and allowed to stand at 4° C. for 3 days. The reaction solution was passed through Sephadex G-25 column (10 mmID×40 cmL, Pharmacia) equilibrated with a solution (pH 8.0) of 20 mM Tris-HCl and 2.5 M urea to collect the fraction of hGH. The obtained fraction was passed through DEAE-5PW column (2.15 cm φ×15 cm, Tosoh) using HPLC method (Gilson HPLC system: Gilson). The column was eluted with using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 7.5 ml/minute of flow rate for 70 minutes to collect hGH fraction.

Working Example 23

Ten mg of Met-ETC having methionine at its N-terminal obtained in Reference Example 4 was dissolved in 4 ml of 3 M urea solution. To the mixture was added a solution (pH 5.0) containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was passed through Sephadex G-25 column (25 mmID×600 mmL) equilibrated with 50 mM phosphate buffer solution (pH 6.0) and the column washed with the same buffer solution at 6 ml/minute of flow rate to collect the fraction of BTC having no methionine at its N-terminal. The collected fraction was adjusted to pH 6.0 and loaded on SP-5PW column (7.5 mmID×75 mmL, Tosoh) equilibrated with 200 mM NaCl and 100 mM phosphate buffer solution (pH 5.0), followed by eluting with a linear concentration gradient of 0–100% solution B (B=100 mM phosphate buffer solution+200 mM NaCl, pH 9.0) at 0.8 ml/minute of flow rate for 30 minutes to collect the fraction of BTC. The collected fraction was passed through ODP-50 column (10 mmID×250 mmL, Showa Denko) equilibrated with 0.1% TFA, followed by eluting with 20–60% B (B=80% acetonitrile/0.1% TFA) at 2 ml/minute of flow rate for 40 minutes to collect the fraction of BTC. The collected fraction was subjected to freeze dry to obtain about 760 μg of BTC.

Working Example 24
(Determination of Feature of BTC)

a) Analysis with SDS-polyacrylamide Gel Electrophoresis

Figure 6:
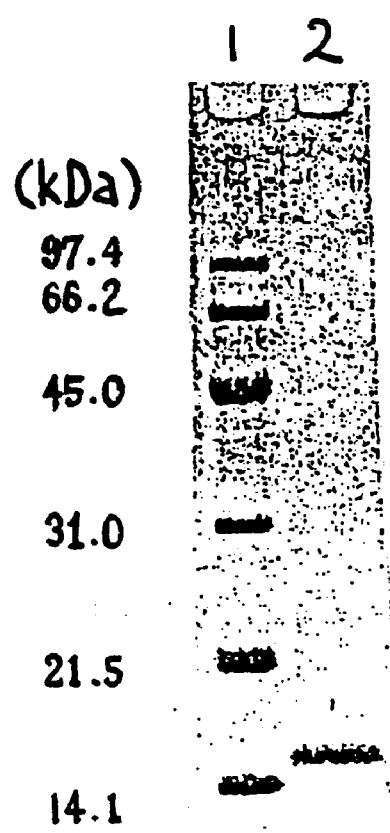
FIG. 6 shows the result of the electrophoresis obtained in Working Example 24a).

To the BTC solution obtained in Working Example 23 was added Sample buffer [Laemmli, Nature, 227, 680 (1970)] containing 100 mM DTT, and the mixture was heated at 95° C. for 1 minute, followed by electrophoresis with Multi Gel 15/25 (Daiichi Pure Chemicals). After electrophoresis, the gel was stained with Coomassie brilliant blue and only one single band at about 16 kd of the purified protein was obtained. It was found from the result that the obtained BTC forms a strong dimer under the reduction condition with DTT. The result is shown in FIG. 6. In FIG. 6, Lanes 1–2 represent molecular weight markers and BTC, respectively.

b) Analysis of N-terminal Amino Acid Sequence

The N-terminal amino acid sequence of BTC obtained in Working Example 23 was determined using a gas-phase protein sequencer (Applied Biosystems, 477A model). The N-terminal amino acid sequence of BTC obtained in Working Example 23 agreed with that predicted from cDNA sequence of BTC. The results are shown in Table 16.

TABLE 16

Analysis of N-terminal amino acid sequence

| Residue No. | PTH[1]-amino acid detected | (pmol) | amino acid predicted from cDNA sequence of BTC |
|---|---|---|---|
| 1 | Asn | (271) | Asn |
| 2 | Gly | (432) | Gly |
| 3 | Asn | (249) | Asn |
| 4 | Ser | (95) | Ser |
| 5 | Thr | (150) | Thr |
| 6 | Arg | (98) | Arg |
| 7 | Ser | (89) | Ser |
| 8 | Pro | (255) | Pro |
| 9 | Glu | (177) | Glu |
| 10 | Thr | (140) | Thr |
| 11 | Asn | (139) | Asn |
| 12 | Gly | (187) | Gly |
| 13 | Leu | (227) | Leu |
| 14 | Leu | (281) | Leu |
| 15 | N.D. | | Cys |
| 16 | Gly | (126) | Gly |
| 17 | Asp | (70) | Asp |
| 18 | Pro | (100) | Pro |
| 19 | Glu | (44) | Glu |
| 20 | Glu | (75) | Glu |

Analysis was carried out using 1 nmol of BTC.
[1]phenylthiohydantoin c) Analysis of Amino Acid Composition About 20 μg of BTC obtained in Working Example 23 was used for the determination of amino acid composition with amino acid analyzer (Beckman 6300E system). The amino acid composition of BTC obtained in Working Example 23 agreed with that predicted from cDNA sequence of BTC. The results are shown in Table 17.

TABLE 17

Analysis of amino acid composition

| Amino acid | Number of residues per 1 mole | Values predicted from cDNA sequence of BTC |
|---|---|---|
| Asx | 7.0 | 7 |
| Thr[1] | 5.9 | 6 |
| Ser[1] | 4.8 | 5 |
| Glx | 9.1 | 9 |
| Pro | 4.0 | 4 |
| Gly | 7.1 | 7 |
| Ala | 4.0 | 4 |
| Cys[2] | N.D. | 8 |
| Val | 4.6 | 4 |
| Met | 0 | 0 |
| Ile | 1.9 | 2 |
| Leu | 3.0 | 3 |
| Tyr | 4.0 | 4 |
| Phe | 3.0 | 3 |
| His | 2.4 | 2 |
| Lys | 5.1 | 5 |
| Arg | 7.0 | 7 |
| Trp[2] | N.D. | 0 |

Acid hydrolysis (6N HCl, 1% phenol, 110° C., Mean value of those obtained after 24 and 48 hours of hydrolysis)
[1]Value extrapolated on the assumption that hydrolysis time was 0 hours.
[2]Undetected d) Analysis of C-terminal Amino Acid About 15 nmol of BTC obtained in Working Example 23 was used for the determination of C-terminal amino acid with amino acid analyzer (Beckman 6300E system). The C-terminal amino acid of BTC obtained in Working Example 23 agreed with that predicted from cDNA sequence of BTC. The results are shown in Table 18.

TABLE 18

Analysis of C-terminal amino acid

| C-terminal amino acid | Yield (%) |
|---|---|
| Tyr | 60.5 |

Vapor-phase Hydrazinolysis (100° C., 3.5 hours)

Working Example 25
(Determination of BTC activity)

Assay of BTC purified and obtained in Working Example 23 was carried out using BALB/c 3T3 A31-714 clone 4 [International Journal of Cancer, 12, 463 (1973)] according to the method described in Molecular Cell Biology, 8, 588 (1988) and revealed that BTC purified and obtained in Working Example 23 had a cell growth enhancing activity almost similar to a standard product (purified BTCI described in Working Example 13 of Japanese Patent Publication Laid-open Number 87894/1994).

Working Example 26

Forty mg of Met-BTC having methionine at its N-terminal obtained in Reference Example 4 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added tolylene-3,4-diamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 27

Forty mg of Met-BTC having methionine at its N-terminal obtained in Reference Example 4 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added 2,3-diaminophenol to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 28

Forty mg of Met-BTC having methionine at its N-terminal obtained in Reference Example 4 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added 3,4-diaminobenzoic acid to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 29

Forty mg of Met-BTC having methionine at its N-terminal obtained in Reference Example 4 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added 4-chloro-o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 30

Forty mg of Met-BTC having methionine at its N-terminal obtained in Reference Example 4 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added cysteamine to give a final concentration of 40 mM and the mixture was adjusted to pH 8.5, followed by vacuum and sealing with nitrogen gas, and the reaction was proceeded at 37° C. for 15 hours. The reaction solution was purified by the same method as described in Working Example 23 to obtain a purified BTC.

Working Example 31

Twenty mg of Met-BTC having methionine at its N-terminal obtained in Reference Example 4 was dissolved in 2 ml of 3 M urea solution. To the mixture was added 2 ml solution containing 4 M sodium acetate, 20 mM acetic acid, 0.4 M glyoxylic acid, 20 mM nickel sulfate and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 32

Twenty mg of Met-BTC having methionine at its N-terminal obtained in Reference Example 4 was dissolved in 2 ml of 3 M urea solution. To the mixture was added 2 ml solution containing 4 M sodium acetate, 20 mM acetic acid, 0.4 M glyoxylic acid, 20 mM cobalt chloride and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 33

Twenty mg of Met-BTC having methionine at its N-terminal obtained in Reference Example 4 was dissolved in 2 ml of 3 M urea solution. To the mixture was added 2 ml solution containing 4 M sodium acetate, 20 mM acetic acid, 0.4 M glyoxylic acid, 20 mM zinc sulfate and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 34

Forty mg of Met-BTC having methionine at its N-terminal obtained in Reference Example 4 was dissolved in 4 ml of 3 M urea solution. To the mixture was added a solution containing 50 mM copper acetate 0.5 ml, 0.25 g glyoxylic acid and 0.5 ml pyridine and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 35

Twenty mg of Met-BTC having methionine at its N-terminal obtained in Reference Example 4 was dissolved in 2 ml of 3 M urea solution. To the mixture was added 2 ml solution containing 4 M sodium acetate, 0.8 mM acetic acid, 0.4 M glyoxylic acid, 10 mM copper sulfate and 3 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 36

Twenty mg of Met-BTC having methionine at its N-terminal obtained in Reference Example 4 was dissolved in 2 ml of 3 M urea solution. To the mixture was added 2 ml solution containing 1 M imidazole, 0.5 M glyoxylic acid, 20 mM copper sulfate and 3 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-BTC. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 23 to obtain a purified BTC.

Working Example 37

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was passed through Sephadex G-25 column (25 mmID×600 mmL) equilibrated with 50 mM phosphate buffer solution (pH 6.0) and the column washed with the same buffer solution at 6 ml/minute of flow rate to collect the fraction of NT-3 having no methionine at its N-terminal. The collected fraction was adjusted to pH 6.0 and loaded on SP-5PW column (21.5 mmID×150 mmL, Tosoh) equilibrated with 200 mM NaCl and 100 mM phosphate buffer solution (pH 5.0), followed by eluting with a linear concentration gradient of 0–100% solution B (B=100 mM phosphate buffer solution+200 mM NaCl, pH 9.0) at 6 ml/minute of flow rate for 55 minutes to collect the fraction of NT-3. The collected fraction was passed through ODP-50 column (10 mmID×250 mmL, Showa Denko) equilibrated with 0.1% TFA, followed by eluting with 20–60% B (B=80% acetonitrile/0.1% TFA) at 2 ml/minute of flow rate for 40 minutes to collect the fraction of NT-3. The collected fraction was subjected to freeze dry to obtain about 600 μg of NT-3.

Figure 7:
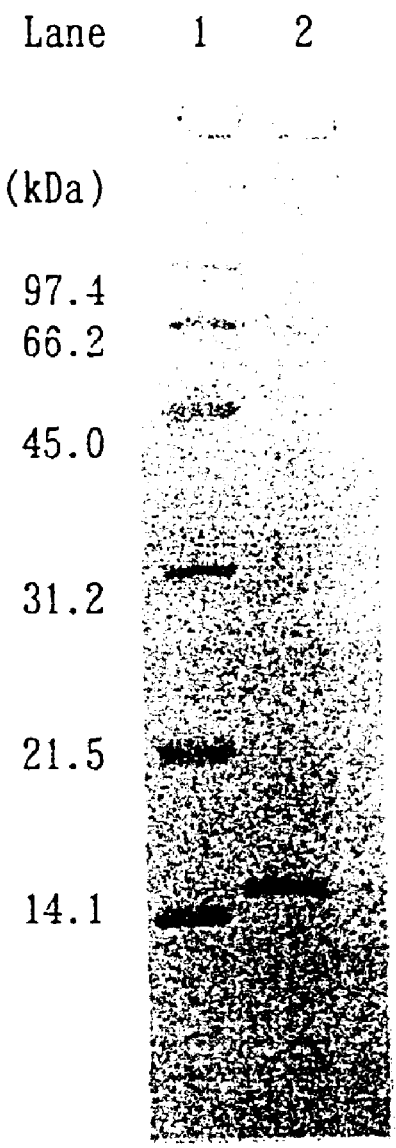
FIG. 7 shows the result of the electrophoresis obtained in Working Example 38a).

Working Example 38
(Determination of Feature of NT-3)
a) Analysis with SDS-polyacrylamide Gel Electrophoresis To the NT-3 solution obtained in Working Example 37 was added Sample buffer [Laemmli, Nature, 227, 680 (1970)] containing 100 mM DTT, and the mixture was heated at 100° C. for 1 minute, followed by electrophoresis with Multi Gel 15/25 (Daiichi Pure Chemicals). After electrophoresis, the gel was stained with Coomassie brilliant blue and only one single band of the purified protein was obtained. The result is shown in FIG. 7. In FIG. 7, Lanes 1–2 represent molecular weight markers and NT-3, respectively.

b) Analysis of N-terminal Amino Acid Sequence

The N-terminal amino acid sequence of NT-3 obtained in Working Example 37 was determined using a gas-phase protein sequencer (Applied Biosystems, 477A model). The N-terminal amino acid sequence of NT-3 obtained in Working Example 37 agreed with that predicted from cDNA sequence of NT-3. The results are shown in Table 19.

TABLE 19

Analysis of N-terminal amino acid sequence

| Residue No. | PTH[1])-amino acid detected | (pmol) | amino acid predicted from cDNA sequence of NT-3 |
| --- | --- | --- | --- |
| 1 | Tyr | (499) | Tyr |
| 2 | Ala | (762) | Ala |
| 3 | Glu | (609) | Glu |
| 4 | His | (371) | His |
| 5 | Lys | (725) | Lys |
| 6 | Ser | (190) | Ser |
| 7 | His | (285) | His |
| 8 | Arg | (254) | Arg |
| 9 | Gly | (474) | Gly |
| 10 | Glu | (373) | Glu |
| 11 | Tyr | (391) | Tyr |
| 12 | Ser | (128) | Ser |
| 13 | Val | (412) | Val |
| 14 | N.D. | | Cys |
| 15 | Asp | (219) | Asp |
| 16 | Ser | (56) | Ser |
| 17 | Glu | (141) | Glu |
| 18 | Ser | (68) | Ser |
| 19 | Leu | (142) | Leu |
| 20 | Trp | (40) | Trp |

Analysis was carried out using 1 nmol of NT-3.
[1])phenylthiohydantoin c) Analysis of Amino Acid Composition About 20 μg of NT-3 obtained in Working Example 37 was used for the determination of amino acid composition with amino acid analyzer (Beckman 6300E system). The amino acid composition of NT-3 obtained in Working Example 37 agreed with that predicted from cDNA sequence of NT-3. The results are shown in Table 20.

TABLE 20

Analysis of amino acid composition

| Amino acid | Number of residues per 1 mole | Values predicted from cDNA sequence of NT-3 |
|---|---|---|
| Asx | 11.1 | 11 |
| Thr[1] | 9.0 | 9 |
| Ser[1] | 12.0 | 12 |
| Glx | 11.0 | 11 |
| Pro | 2.0 | 2 |
| Gly | 7.8 | 8 |
| Ala | 4.7 | 5 |
| Cys[2] | N.D. | 6 |
| Val | 9.0 | 9 |
| Met | 0 | 0 |
| Ile | 6.6 | 7 |
| Leu | 5.1 | 5 |
| Tyr | 4.8 | 5 |
| Phe | 0.9 | 1 |
| His | 4.1 | 4 |
| Lys | 10.0 | 10 |
| Arg | 9.8 | 10 |
| Trp[2] | N.D. | 4 |

Acid hydrolysis (6N HCl, 1% phenol, 110° C., Mean value of those obtained after 24 and 48 hours of hydrolysis)
[1]Value extrapolated on the assumption that hydrolysis time was 0 hours.
[2]Undetected d) Analysis of C-terminal Amino Acid About 15 nmol of NT-3 obtained in Working Example 37 was used for the determination of C-terminal amino acid with amino acid analyzer (Beckman 6300E system). The C-terminal amino acid of NT-3 obtained in Working Example 37 agreed with that predicted from cDNA sequence of NT-3. The results are shown in Table 21.

TABLE 21

Analysis of C-terminal amino acid

| C-terminal amino acid | Yield (%) |
|---|---|
| Thr | 42.0 |

Vapor-phase Hydrazinolysis (100° C., 3.5 hours)

Working Example 39
(Determination of NT-3 activity)

Assay of NT-3 purified and obtained in Working Example 37 was carried out using DRG and revealed that NT-3 purified and obtained in Working Example 37 had an activity almost similar to NT-3 obtained from CHO cells.

Working Example 40

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added tolylene-3,4-diamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 41

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added 2,3-diaminophenol to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 42

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added 3,4-diaminobenzoic acid to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 43

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added 4-chloro-o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 44

Forty mg of Met-NT-3 having methionine at its N-terminal obtained in Reference Example 3 was dissolved in 4 ml of 3 M urea solution. To the mixture was added a solution containing 50 mM copper sulfate 0.5 ml, glyoxylic acid 0.25 g and pyridine 0.5 ml and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added cysteamine to give a final concentration of 40 mM and the mixture was adjusted to pH 8.5, followed by vacuum and sealing with nitrogen gas, and the reaction was proceeded at 37° C. for 15 hours. The reaction solution was purified by the same method as described in Working Example 37 to obtain a purified NT-3.

Working Example 45

Twenty mg of Met-NT-3 having methionine at its N-terminal obtained in Reference Example 3 was dissolved in 2 ml of 3 M urea solution. To the mixture was added 2 ml solution containing 4 M sodium acetate, 20 mM acetic acid, 0.4 M glyoxylic acid, 20 mM nickel sulfate and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 46

Twenty mg of Met-NT-3 having methionine at its N-terminal obtained in Reference Example 3 was dissolved in 2 ml of 3 M urea solution. To the mixture was added 2 ml solution containing 4 M sodium acetate, 20 mM acetic acid, 0.4 M glyoxylic acid, 20 mM cobalt chloride and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 47

Twenty mg of Met-NT-3 having methionine at its N-terminal obtained in Reference Example 3 was dissolved in 2 ml of 3 M urea solution. To the mixture was added 2 ml solution containing 4 M sodium acetate, 20 mM acetic acid, 0.4 M glyoxylic acid, 20 mM zinc sulfate and 6 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 48

Forty mg of Met-NT-3 having methionine at its N-terminal obtained in Reference Example 3 was dissolved in 4 ml of 3 M urea solution. To the mixture was added a solution containing 50 mM copper acetate 0.5 ml, 0.25 g glyoxylic acid and 0.5 ml pyridine and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 49

Twenty mg of Met-NT-3 having methionine at its N-terminal obtained in Reference Example 3 was dissolved in 2 ml of 3 M urea solution. To the mixture was added 2 ml solution containing 4 M sodium acetate, 0.8 mM acetic acid, 0.4 M glyoxylic acid, 10 mM copper sulfate and 3 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C. for 15 hours. The reaction solution was purified by the same method as described in Working Example 37 to obtain a purified NT-3.

Working Example 50

Twenty mg of Met-NT-3 having methionine at its N-terminal obtained in Reference Example 3 was dissolved in 2 ml of 3 M urea solution. To the mixture was added 2 ml solution containing 1 M imidazole, 0.5 M glyoxylic acid, 20 mM copper sulfate and 3 M urea and allowed to stand at 25° C. for 1 hour. The reaction solution was passed through Sephadex G-25 column (25 mmID×600 mmL) equilibrated with 2.5 M urea and 50 mM phosphate buffer solution (pH 6.0) and the column was washed with the same buffer solution at 6 ml/minute of flow rate to collect the fraction of diketone derivative of Met-NT-3. To this fraction was added the same volume of 4 M acetic acid-4 M sodium acetate solution and then added o-phenylenediamine to give a final concentration of 40 mM, followed by vacuum and sealing with nitrogen gas, and the reaction was proceeded at 37° C.

for 15 hours. The reaction solution was purified by the same method as described in Working Example 37 to obtain a purified NT-3.

Activation of denatured Met-NT-3 and Purification of activated Met-NT-3 can be carried out, for example, by the following method. That is, the pellet solution obtained in Reference Example 3(5) is centrifuged (10000 rpm) and the obtained supernatant was diluted to about 20 times volume with 100 mM phosphate buffer solution (pH 8.5) containing 1.8 M urea, 0.2 M Arg, 0.2 mM GSSG and 1.0 mM GSH. The mixture is allowed to stand at 4° C. for 4 weeks to proceed refolding (activation) of denatured Met-NT-3.

After the refolding, the solution is adjusted to pH 6.0 and loaded on SP-Sepharose column (22 mmID×120 mmL) equilibrated with 100 mM phosphate buffer solution (pH 6.0), followed by eluting with 100 mM phosphate buffer solution+400 mM NaCl (pH 6.0) to collect the fraction of Met-NT-3. The collected fraction is passed through ODP-50 column (21.5 mmID×300 mmL, Showa Denko) equilibrated with 0.1% TFA, followed by eluting with 0–80% B (B=acetonitrile/0.1% TFA) at 5 ml/minute of flow rate for 60 minutes to collect the fraction of Met-NT-3. The collected fraction is subjected to freeze dry to obtain powder of Met-NT-3.

Citrulline, Ala, Val, Asp, etc. can be used for the refolding, instead of the above described Arg.

Working Example 51

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added 3.375 ml solution containing 1.55 g glyoxylic acid, 0.1 M nickel chloride, 4 M sodium acetate, 20 mM acetic acid and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 52

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added 3.375 ml solution containing 1.55 g glyoxylic acid, 0.1 M cobalt chloride, 4 M sodium acetate, 20 mM acetic acid and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 53

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added 3.375 ml solution containing 1.55 g glyoxylic acid, 0.1 M zinc sulfate, 4 M sodium acetate, 20 mM acetic acid and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 54

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added 3.375 ml solution containing 1.55 g glyoxylic acid, 0.1 M copper acetate, 4 M sodium acetate, 20 mM acetic acid and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 55

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added a solution containing 1.55 g glyoxylic acid, 0.1 M copper sulfate 3.375 ml and pyridine 3.375 ml and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. This fraction was adjusted to pH 8.5 and to this fraction was added cysteamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 56

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added a solution containing 1.55 g glyoxylic acid, 0.1 M copper sulfate 3.375 ml and pyridine 3.375 ml and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added tolylene-3,4-diamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 57

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added a solution containing 1.55 g glyoxylic acid, 0.1 M copper sulfate 3.375 ml and pyridine 3.375 ml and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added 4-chloro-o-phenylenediamine to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 58

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added a solution containing 1.55 g glyoxylic acid, 0.1 M copper sulfate 3.375 ml and pyridine 3.375 ml and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added 3,4-diaminobenzoic acid to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 59

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added a solution containing 1.55 g glyoxylic acid, 0.1 M copper sulfate 3.375 ml and pyridine 3.375 ml and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added 2,3-diaminophenol to give a final concentration of 40 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 60

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added the same volume of a solution containing 0.5 M glyoxylic acid, 20 mM zinc sulfate, 40 mM ammonium acetate buffer solution (pH 5.0) and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 61

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added the same volume of a solution containing 0.5 M glyoxylic acid, 20 mM copper acetate, 40 mM ammonium acetate buffer solution (pH 5.0) and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 62

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added the same volume of a solution containing 0.5 M glyoxylic acid, 20 mM nickel chloride, 40 mM ammonium acetate buffer solution (pH 5.0) and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 63

Twenty mg of human interleukin-2 (Met-IL-2) having methionine at its N-terminal obtained in Reference Example 5 was dissolved in 27 ml of 20 mM ammonium acetate buffer solution (pH 5.0). To the mixture was added the same volume of a solution containing 0.5 M glyoxylic acid, 20 mM cobalt chloride, 40 mM ammonium acetate buffer solution (pH 5.0) and 6 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 64

Twenty mg of human interleukin-2 (Met-IL-2) having methionine at its N-terminal obtained in Reference Example 5 was dissolved in 27 ml of 20 mM ammonium acetate buffer solution (pH 5.0), followed by dialysis against 2 l solution of 20 mM Tris-HCl (pH 8.0) containing 3 M urea. To the dialyzed solution was added the same volume of a solution containing 1 M imidazole, 0.5 M glyoxylic acid, 20 mM copper sulfate and 2.5 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Working Example 65

Twenty mg of human interleukin-2 (Met-IL-2) having methionine at its N-terminal obtained in Reference Example 5 was dissolved in 27 ml of 20 mM ammonium acetate buffer solution (pH 5.0), followed by dialysis against 2 l solution of 20 mM Tris-HCl (pH 8.0) containing 3 M urea. To the dialyzed solution was added the same volume of a solution containing 4 M sodium acetate, 0.4 M glyoxylic acid, 10 mM copper sulfate, 0.8 M acetic acid and 2.5 M urea and allowed to stand at room temperature for 1 hour. The reaction solution was passed at 300 ml/h of flow rate through Sephadex G-25 column (25 mmID×600 mmL) equilibrated with 20 mM ammonium acetate buffer solution (pH 5.0) to collect the fraction of diketone derivative of Met-IL-2. To this fraction was added o-phenylenediamine to give a final concentration of 20 mM, followed by vacuum and sealing with nitrogen gas, and the reaction was proceeded at 37° C. for 21 hours. The reaction solution was treated by the same method as described in Working Example 8 to obtain freeze-dried powder of IL-2.

Reference Example 10

*Escherichia coli* MM294 (DE3)/pE-C35PTH [IFO 15213] disclosed in EP-A-499990 and JP-A-304976/1993 was inoculated into 1 liter of liquid medium (pH 7.0) containing 1% Bacto TRYPTONE, 0.5% yeast extract, 0.5% sodium chloride and 50 μg/ml ampicillin and then subjected to rotary shaking cultivation at 30° C. The resultant culture liquid 1 liter was then transferred to 19 liter of liquid medium (pH 7.0) containing 1% Bacto TRYPTONE, 0.5% yeast extract and 0.5% sodium chloride and then subjected to cultivation under aeration and agitation at 30° C. for 8 hours. The resultant culture liquid 17 liter was then transferred to a 500 liter jar fermentor containing 343 liter of M-9 medium [0.0005% vitamin $B_1$, 1.5% glucose, 1.5% casamino acid], after which it was subjected to cultivation under aeration and agitation at 37° C. for 7 hours to obtain about 350 l of culture liquid. The obtained culture liquid was centrifuged to obtain about 4 kg of wet cells which were frozen at −80° C.

Reference Example 11

To 10 g of wet cells obtained in Reference Example 10 was added 20 mM ammonium acetate buffer solution 40 ml (pH 5.0) containing 7 M guanidine hydrochloride and the cells were dissolved in the solution, followed by centrifugation (10000 rpm, 60 minutes) to obtain about 40 ml of cell extract. The cell extract was diluted with about 2 l of 20 mM ammonium acetate buffer solution (pH 5.0), followed by centrifugation (4200 rpm, 20 minutes) to obtain about 2 l of the resultant supernatant. The supernatant was loaded on SP-Toyopearl 650M column (5 cm φ×30 cm), followed by adsorption and washing. The column was eluted with 20 mM ammonium acetate buffer solution (pH 5.0) containing 1 M NaCl. The eluted solution was loaded on ODS-120T column (21.5 cm φ×30 cm, Tosoh) using HPLC method, followed by elution with a linear concentration gradient consisting of (1) 0.1% TFA and (2) 80% acetonitrile containing 0.1% TFA to obtain about 30 ml fraction of Met-[$Cys^{35}$]-PTH(1-84). The fraction was dialyzed against 0.1 M acetic acid solution (5l) containing 6 M urea. To the resultant solution was added about 4 mg of DMAP-CN [1-cyano-4-dimethylaminopyridinium tetrafluoborate] and the solution was allowed to stand at room temperature for 15 minutes to obtain Met-[$Cys(CN)^{35}$]PTH(1-84). The obtained reaction solution was loaded on SP-Toyopearl 650M column (1.0 cm φ×30 cm) and the column was washed with 20 mM ammonium acetate buffer solution (pH 5.0) containing 100 mM NaCl to remove the reaction agent, followed by elution with 20 mM ammonium acetate buffer solution (pH 5.0) containing 1 M NaCl. The eluted solution was dialyzed against 5 l solution of 6 M urea. The resultant solution (about 8 ml) was ice-cooled, to which about 400 μl of 1 N NaOH, and the mixture was allowed to stand at 0° C. for 10 minutes. The resultant reaction solution was subjected to gel filtration with Toyopearl HW-50F (2 cm φ×50 cm) equilibrated with 20 mM ammonium acetate buffer solution (pH 5.0) to collect the fraction of Met-PTH(1-34). The fraction was loaded on ODS-120T column (21.5 cm φ×30 cm, Tosoh) using HPLC method, followed by elution with a linear concentration gradient consisting of (1) 0.1% TFA and (2) 80% acetonitrile containing 0.1% TFA to obtain about 50 ml fraction of Met-PTH(1-34). The fraction was subjected to freeze drying to obtain about 5 mg of Met-PTH(1-34).

Working Example 66

Five mg of Met-PTH(1-34) having methionine at its N-terminal obtained in Reference Example 11 was dissolved in 1 ml of distilled water. To the mixture was added a solution containing 46.4 mg glyoxylic acid, 2.5 mg copper sulfate and 94.8 mg pyridine, and the mixture was allowed to stand at room temperature for 1 hour. The reaction solution was centrifuged and the obtained supernatant was loaded on ODP-50 column (1 cm φ×25 cm, Showa Denko) using HPLC method, followed by elution with a linear concentration gradient consisting of (1) 20 mM ammonium acetate buffer solution (pH 5.0) containing 10% acetonitrile and (2) 20 mM ammonium acetate buffer solution (pH 5.0) containing 60% acetonitrile to obtain about 5.4 ml fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the mixture was allowed to stand at 37° C. for 17 hours. The reaction solution was loaded on ODP-50 column (1 cm φ×25 cm, Showa Denko) using HPLC method, followed by elution with a linear concentration gradient consisting of (1) 0.1% TFA and (2) 80% acetonitrile containing 0.1% TFA to obtain the fraction of PTH(1-34). The fraction was diluted 5 times with 20 mM ammonium acetate buffer solution (pH 5.0) and the diluted solution was loaded on SP-5PW column (7.5 mm φ×75 mm, Tosoh) equilibrated with 20 mM ammonium acetate buffer solution (pH 5.0) containing 2 M urea, followed by elution with a linear concentration gradient consisting of 0–50% solution B (B=20 mM MES, 2 M urea and 0.5 M NaCl) at 0.8 ml/minute of flow rate for 30 minutes to collect the fraction of PTH(1-34), which was dialyzed against 1 l of distilled water. The dialyzed solution was subjected to freeze drying to obtain freeze-dried powder of PTH(1-34).

Working Example 67
(Determination of Feature of PTH(1-34))

a) Analysis with SDS-polyacrylamide Gel Electrophoresis

Figure 8:
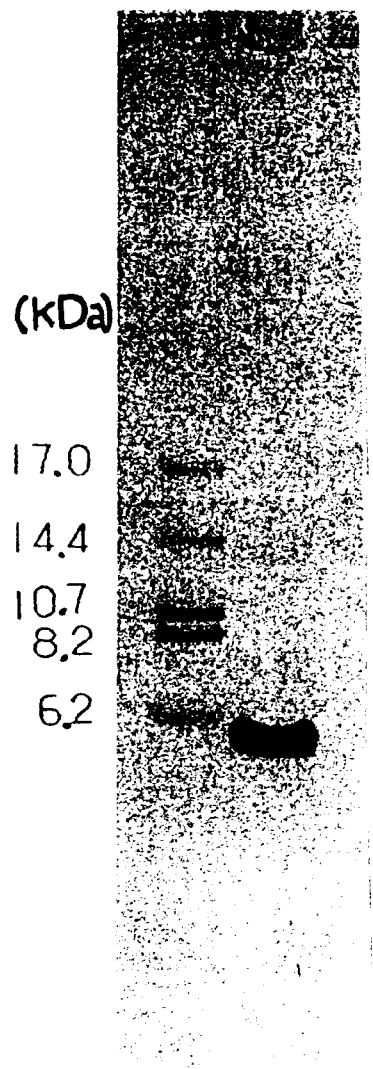
FIG. 8 shows the result of the electrophoresis obtained in Working Example 67a).

The PTH(1-34) powder obtained in Working Example 66 was suspended in Sample buffer [NOVEX JAPAN], and the mixture was subjected to electrophoresis with Peptide-PAGE mini [TEFCO]. After electrophoresis, the gel was stained with Coomassie brilliant blue and only one single band of the purified protein was obtained. The result is shown in FIG. 8. In FIG. 8, Lanes 1–2 represent molecular weight markers and PTH(1-34), respectively.

b) Analysis of N-terminal Amino Acid Sequence

The N-terminal amino acid sequence of PTH(1-34) obtained in Working Example 66 was determined using a gas-phase protein sequencer (Applied Biosystems, 477A model). The N-terminal amino acid sequence of PTH(1-34) obtained in Working Example 66 agreed with that predicted from cDNA sequence of PTH(1-34). The results are shown in Table 22.

TABLE 22

Analysis of N-terminal amino acid sequence

| Residue No. | PTH[1]-amino acid detected | (pmol) | amino acid predicted from cDNA sequence of PTH (1–34) |
|---|---|---|---|
| 1 | Ser | (71) | Ser |
| 2 | Val | (243) | Val |
| 3 | Ser | (91) | Ser |
| 4 | Glu | (139) | Glu |
| 5 | Ile | (198) | Ile |
| 6 | Gln | (55) | Gln |
| 7 | Leu | (86) | Leu |
| 8 | Met | (118) | Met |
| 9 | His | (34) | His |
| 10 | Asn | (95) | Asn |
| 11 | Leu | (135) | Leu |
| 12 | Gly | (77) | Gly |
| 13 | Lys | (50) | Lys |
| 14 | His | (30) | His |
| 15 | Leu | (103) | Leu |
| 16 | Asn | (40) | Asn |
| 17 | Ser | (29) | Ser |
| 18 | Met | (36) | Met |
| 19 | Glu | (35) | Glu |
| 20 | Arg | (27) | Arg |

Analysis was carried out using 400 pmol of PTH (1–34).
[1]phenylthiohydantoin c) Analysis of Amino Acid Composition PTH(1-34) obtained in Working Example 66 was used for the determination of amino acid composition with amino acid analyzer (Hitachi L-8500A Amino Acid Analyzer). The amino acid composition of PTH(1-34) obtained in Working Example 66 agreed with that predicted from cDNA sequence of PTH(1-34). The results are shown in Table 23.

TABLE 23

Analysis of amino acid composition

| Amino acid | Number of residues per 1 mole | Values predicted from cDNA sequence of PTH (1–34) |
|---|---|---|
| Asx | 4.0 | 4 |
| Thr | 0 | 0 |
| Ser | 2.8 | 3 |
| Glx | 4.9 | 5 |
| Pro | 0 | 0 |
| Gly | 1.0 | 1 |
| Ala | 0 | 0 |
| Cys[1] | — | 0 |
| Val | 2.9 | 3 |
| Met | 2.0 | 2 |
| Ile | 0.9 | 1 |
| Leu | 5.0 | 5 |
| Tyr | 0 | 0 |
| Phe | 1.0 | 1 |
| His | 3.0 | 3 |
| Lys | 2.9 | 3 |
| Arg | 2.0 | 2 |
| Trp | 1.0 | 1 |

Acid hydrolysis (6N HCl, 1% thioglycolic acid, 110° C., 24 hours of hydrolysis)
[1]Undetected d) Analysis of C-terminal Amino Acid PTH(1-34) obtained in Working Example 66 was used for the determination of C-terminal amino acid with amino acid analyzer (Hitachi L-8500A Amino Acid Analyzer). The C-terminal amino acid of rPTH(1-34) obtained in Working Example 66 agreed with that predicted from cDNA sequence of PTH(1-34). The results are shown in Table 24.

TABLE 24

Analysis of C-terminal amino acid

| C-terminal amino acid | Yield (%) |
|---|---|
| Phe | 94.4 |

Vapor-phase Hydrazinolysis (100° C., 6 hours)

e) Determination of PTH(1-34) Activity

Assay of PTH(1-34) obtained in Working Example 66 was carried out using MC3T3-E1 cells (osteoblast-like strain) according to the method described in Shizue Nakagawa et al., Biochemical and Biophysical Research Communications, 200, 1735 (1994) and revealed that PTH (1-34) obtained in Working Example 66 had an activity almost similar to a standard product.

Working Example 68

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM nickel chloride and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 69

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM cobalt chloride and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 70

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM zinc sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 71

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper acetate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 72

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml solution of 50 mM Tris-HCl (pH 8.5). To the mixture was added cysteamine to give a final concentration of 40 mM, followed by vacuum and sealing with nitrogen gas, and the reaction solution was allowed to stand treated by the same method as described in Working Example 66 to obtain freeze-dried powder of PTH(1-34).

Working Example 73

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM tolylene-3,4-diamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 74

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM 4-chloro-o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 75

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM 3,4-diaminobenzoic acid, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 76

Five mg of Met-PTH(1-34) having methionine at its N-terminal obtained in Reference Example 11 was dissolved in 1 ml solution of 4 M urea. To the mixture was added 1 ml solution containing 4 M ammonium acetate, 20 mM acetic acid, 0.4 M glyoxylic acid, 20 mM copper sulfate and 4 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM 2,3-diaminophenol, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 77

Five mg of Met-PTH(1-34) having methionine at its N-terminal obtained in Reference Example 11 was dissolved in 1 ml solution of 3 M urea and 20 mM Tris-HCl (pH 8.0). To the mixture was added 1 ml solution containing 1 M imidazole, 0.5 M glyoxylic acid, 20 mM copper sulfate and 2.5 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

Working Example 78

Five mg of Met-PTH(1-34) having methionine at its N-terminal obtained in Reference Example 11 was dissolved in 1 ml solution of 3 M urea and 20 mM Tris-HCl (pH 8.0). To the mixture was added 1 ml solution containing 4 M sodium acetate, 0.8 M acetic acid, 0.4 M glyoxylic acid, 10 mM copper sulfate and 2.5 M urea, and the mixture was allowed to stand at room temperature for 1 hour. The reaction solution was centrifuged and the obtained supernatant was purified by HPLC method using ODP-50 column as described in Working Example 66 to obtain fraction of the diketone derivative of Met-PTH(1-34). The fraction was subjected to freeze dry, to which was added 4 ml of distilled water. To the mixture was added 4 ml solution containing 80 mM o-phenylenediamine, 4 M acetic acid and 4 M ammonium acetate, followed by vacuum and sealing with nitrogen gas, and the reaction solution was allowed to stand treated by the same method as described in Working Example 66 to obtain freeze-dried powder of PTH(1-34).

What is claimed is:

1. A method for removing an oxidized or unoxidized N-terminal methionine residue from a recombinantly produced polypeptide to form a bioactive polypeptide, comprising reacting a polypeptide, or a salt thereof, having said methionine residue at its N-terminus, with a glyoxcylic acid or a salt thereof in the presence of a transition metal ion and a base, and subjecting the obtained product to hydrolysis, and recovering the resultant product to obtain a bioactive polypeptide without its N-terminal methionine residue.

2. The method according to claim 1, wherein the bioactive polypeptide is selected from the group consisting of growth hormone, neutrophin-3, betacellulin, parathyroid hormone and interleukin-2.

3. The method according to claim 1, wherein the transition metal ion is a copper ion.

4. The method according to claim 1, wherein the base is a pyridine.

5. The method according to claim 1, wherein the hydrolysis is carried out by using a base.

6. The method according to claim 5, wherein the base is an amine.

7. The method according to claim 5, wherein the base is (1) a diamine or (2) a thio- or seleno-semicarbazide.

8. The method according to claim 7, wherein the diamine is o-phenylenediamine.

9. The method of claim 5, wherein the base is an alkylamine.

10. The method of claim 5, wherein the base is an aromatic amine.

11. The method of claim 1, where the bioactive polypeptide is selected from the group of: growth hormone, parathyroid hormone, insulin, nerve growth factor, brain-derived neurotrophic factor, ciliary neurotrophic factor, glial derived neurotrophic factor, neurotrophin-3, 4, or 6, central nerve growth factor, gliocyte growth factor, lung-derived neurotrophic factor, epidermal growth factor, fibroblast growth factor, platelet-derived growth factor, transforming growth factor α or β, endothelial cell growth factor, tissue plasminogen activator, urokinase, protein C, thrombomodulin, bone morphogenetic protein, calcitonin, insulin-like growth hormone, interferon-α, β or γ, interleukin-1(α, β) to 12, granulocyte colony stimulating factor, granulocyte macrophage colony stimulating factor, granulocyte macrophage stimulating factor, thrombopoietin, somatomedin C, erytropoietin, PACAP, atrial natriuretic peptide, endothelin, megakaryocyte growth factor, hematopoietic stem cell growth factor, hepatocyte growth factor, motilin, immunotoxin, tumor necrosis factor, hirudine, corticotropin, angiotensin, angiotensin 2 and angiotensin 2-antagonistic peptides, angiotensin 3, bradykinin derivatives, bradykinin enhancing factor, α, β or γ-endorphin, enkephalin, neutrophil chemotactic factor, gastrin, glucagon, growth hormone-releasing factor, kyotorphin, kallidin, gonadotropic hormone releasing hormone, mast cell degranulating peptide, melanocyte stimulating hormone, neurotensin, trypsin inhibitor, oxytocin, proinsulin C-peptide, secretin, somatostatin, thyroid-stimulating hormone releasing hormone, ubiquitin, urogastrone, vasopressin derivatives, kinin derivatives, tuftsin, somatomedin, corticotropin releasing factor, insulin-like grow factor, calcitonin gene related peptide, PTHrP, VIP, DHI, insulinotropiin, GRP, CCK-PZ, Galanin, Antrum Peptide, motilin, PPY, Pancreatic Polypeptide, PSP, pancreastatin, hCG, hCS, relaxin, serum thymic factor, thymopoietin, thymosin, Factor XIII, Factor VIII, prourokinase, SOD, Factor VIIa, antithrombin, betacellulin, and a mutein thereof.

12. A method for producing a bioactive peptide without a methionine residue at its N-terminus, wherein the bioactive peptide is selected from the group consisting of human growth hormone, neutrophin-3, human betacellulin, parathyroid hormone, human interleukin-2 and salts thereof, which comprises reacting a recombinantly produced bioactive peptide or a salt thereof having a methionine at its N-terminus with a glyoxylic acid or a salt thereof in the presence of cupric sulphate and pyridine and then reacting with an o-phenylenediamine to obtain a bioactive peptide without its N-terminal methionine residue.

13. A compound of the formula:

Wherein m is an integer from 0–2 and X is a peptide chain which consists of at least 2 amino acid residues and comprises a part of a protein produced by gene recombination technology, or a salt thereof.

14. A method for producing a peptide or a salt thereof, which comprises subjecting the compound according to claim 13 to hydrolysis and thereafter recovering, the resultant product to obtain a product without an N-terminal methionine.

* * * * *

UNITED STATES PATENT AND TRADEMARK OFFICE

CERTIFICATE OF CORRECTION

PATENT NO.: 6,066,470

DATED: May 23, 2000

INVENTOR(S): O. Nishimura, et al.

It is certified that error appears in the above-identified patent and that said Letters Patent is hereby corrected as shown below:

At column 58, line 15, correct the word "grow" to "growth"

Signed and Sealed this

Third Day of April, 2001

Attest:

NICHOLAS P. GODICI

*Attesting Officer*  *Acting Director of the United States Patent and Trademark Office*